US011850404B2

(12) United States Patent
Basile et al.

(10) Patent No.: US 11,850,404 B2
(45) Date of Patent: *Dec. 26, 2023

(54) MANUALLY-ACTUATED INJECTION DEVICE FOR HIGH-VISCOSITY DRUGS

(71) Applicant: Merck Sharp & Dohme Corp., Rahway, NJ (US)

(72) Inventors: Peter A. Basile, Prattsburgh, NY (US); Henry J. Mack, Jr., Phillipsburg, NJ (US); Oliver Sha, West Islip, NY (US); Stephen G. Miggels, Lake Pleasant, NY (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 240 days.

This patent is subject to a terminal disclaimer.

(21) Appl. No.: 17/495,199

(22) Filed: Oct. 6, 2021

(65) Prior Publication Data

US 2022/0080128 A1  Mar. 17, 2022

Related U.S. Application Data

(63) Continuation of application No. 16/462,354, filed as application No. PCT/US2017/062560 on Nov. 20, 2017, now Pat. No. 11,173,250.
(Continued)

(51) Int. Cl.
*A61M 5/315* (2006.01)
*A61M 5/24* (2006.01)
(Continued)

(52) U.S. Cl.
CPC .......... *A61M 5/31511* (2013.01); *A61M 5/24* (2013.01); *A61M 5/31* (2013.01); *A61M 5/315* (2013.01); *A61M 5/46* (2013.01)

(58) Field of Classification Search
CPC .... A61M 5/31511; A61M 5/31; A61M 5/315; A61M 5/24; A61M 5/46; A61M 5/31586; A61M 5/31581
See application file for complete search history.

(56) References Cited

U.S. PATENT DOCUMENTS 1,718,596 A   6/1929  Smith
4,444,560 A   4/1984  Jacklich
(Continued)

FOREIGN PATENT DOCUMENTS

WO   2016091841 A1   6/2016

OTHER PUBLICATIONS

Unknown, "Mechanical Advantage of a Lever with Formula," PhysicsTeacher.in, Feb. 2017.

*Primary Examiner* — Bradley J Osinski
(74) *Attorney, Agent, or Firm* — Grady L. White; Potomac Law Group, PLLC

(57) ABSTRACT

A manually actuated drug-injecting device is configured such that the grip strength of the entire hand (i.e., majority of fingers closing toward the palm or heel of the hand) is employed to discharge medication through a hypodermic needle and into a patient's body. The device is well suited for delivering medications with high viscosity and/or by patients (e.g., elderly patients) with reduced finger strength and dexterity. The device includes a grip member, a push member (which causes the medication to be injected), and a force-transfer mechanism that couples the grip member to the push member. Suitably, the device is configured to be held transverse to the palm of the medication-administering hand, with a discharge port located by the outer, blade edge of the administering hand, when the device is being gripped to administer medication.

9 Claims, 22 Drawing Sheets

Related U.S. Application Data

(60) Provisional application No. 62/424,746, filed on Nov. 21, 2016.

(51) Int. Cl.
  *A61M 5/46*   (2006.01)
  *A61M 5/31*   (2006.01)

(56) References Cited

U.S. PATENT DOCUMENTS

| | | |
|---|---|---|
| 4,710,172 A | 12/1987 | Jacklich et al. |
| 6,616,448 B2 | 9/2003 | Friedman |
| 2003/0150875 A1 | 8/2003 | Belanger |
| 2011/0160674 A1 | 6/2011 | Holmes et al. |
| 2012/0226261 A1 | 9/2012 | Barnett et al. |

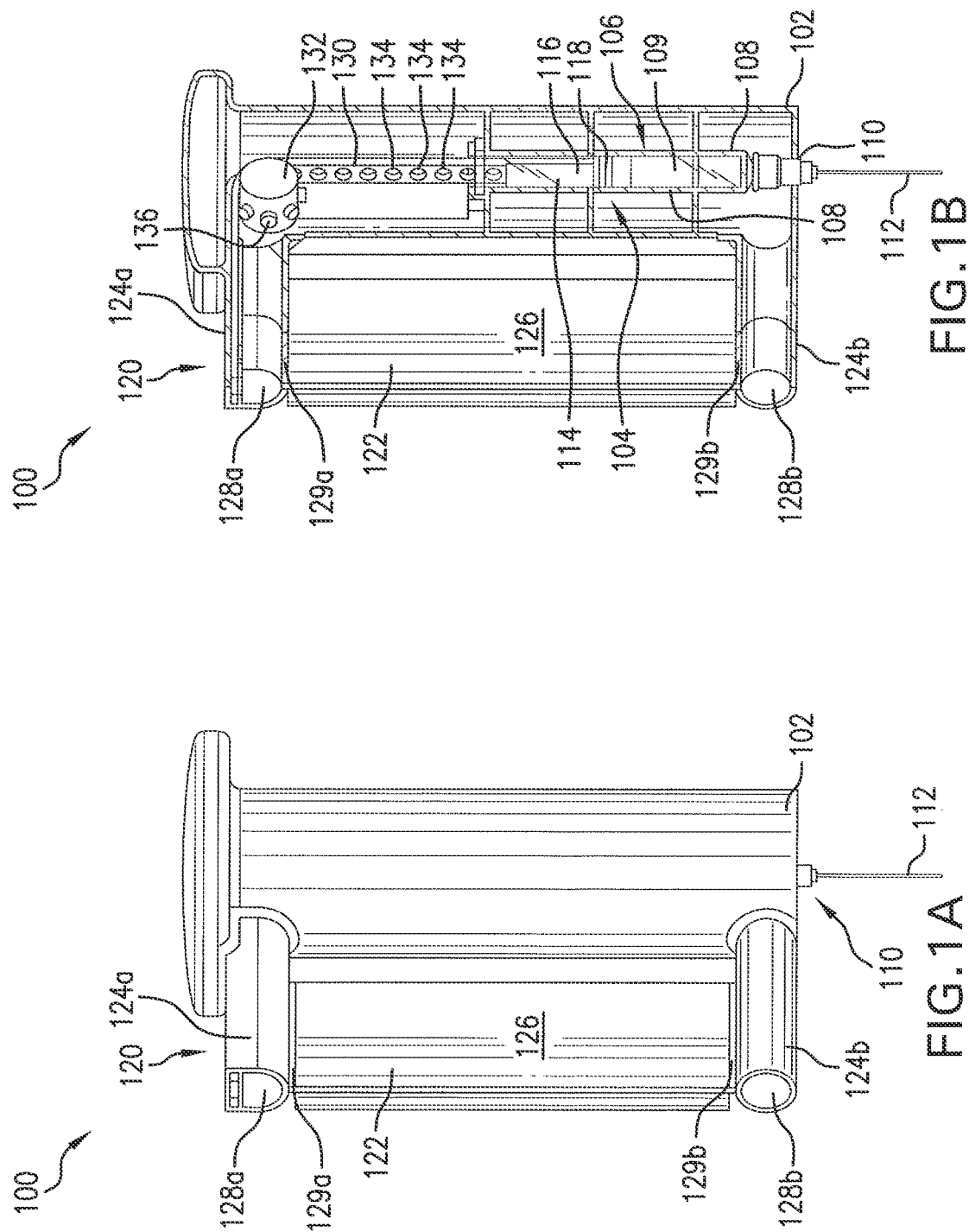

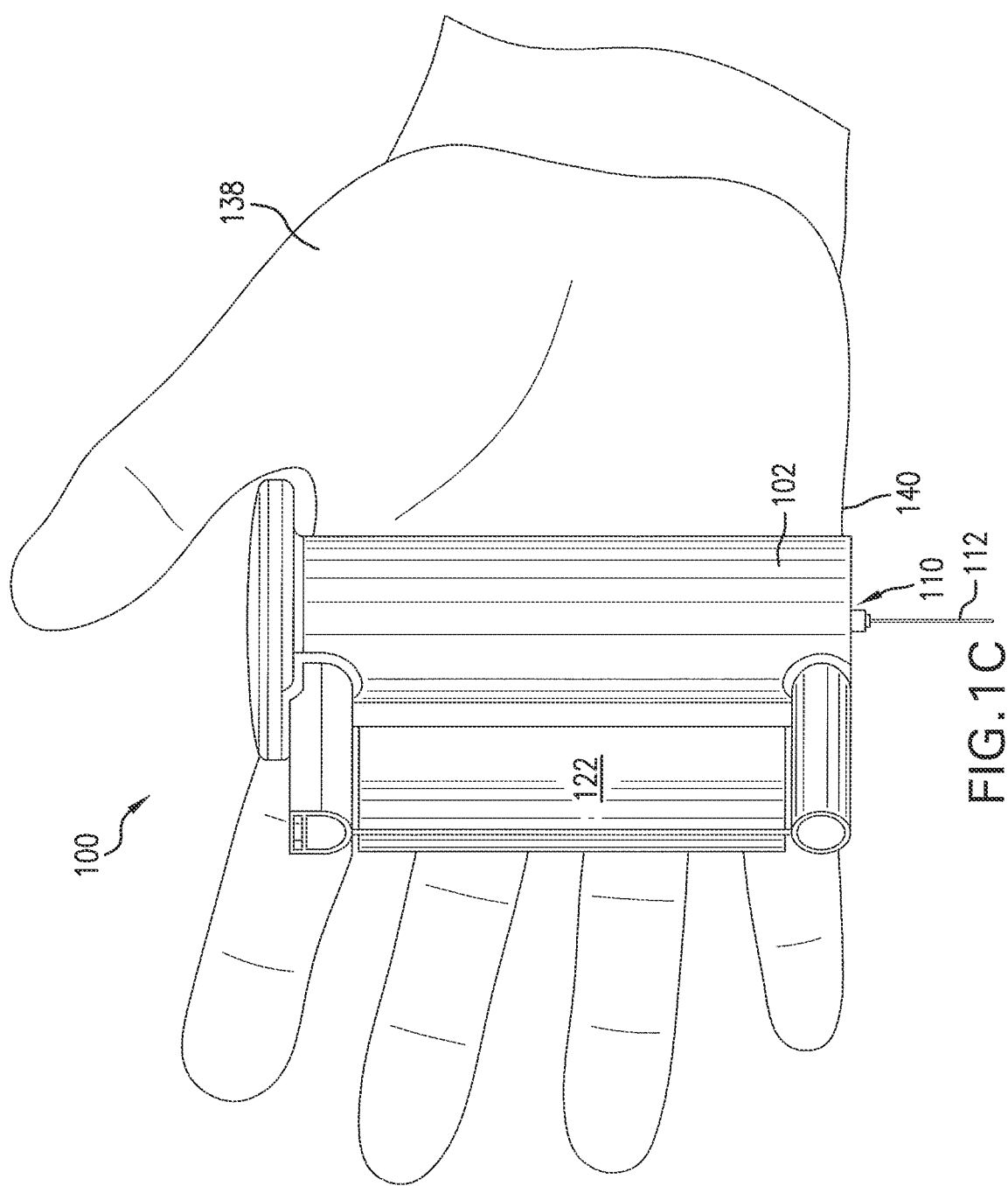

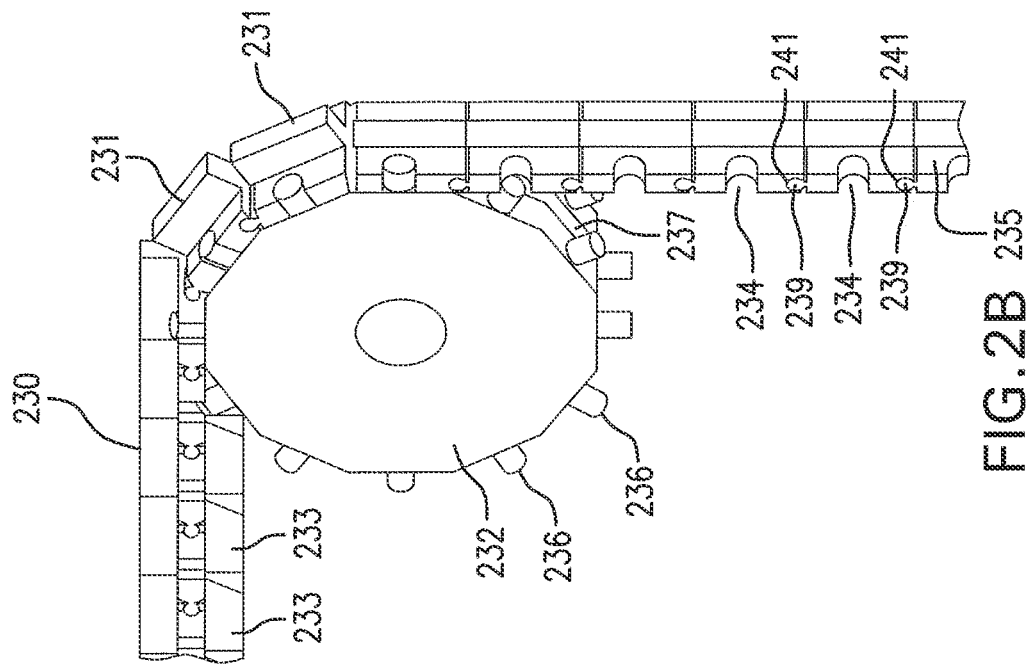
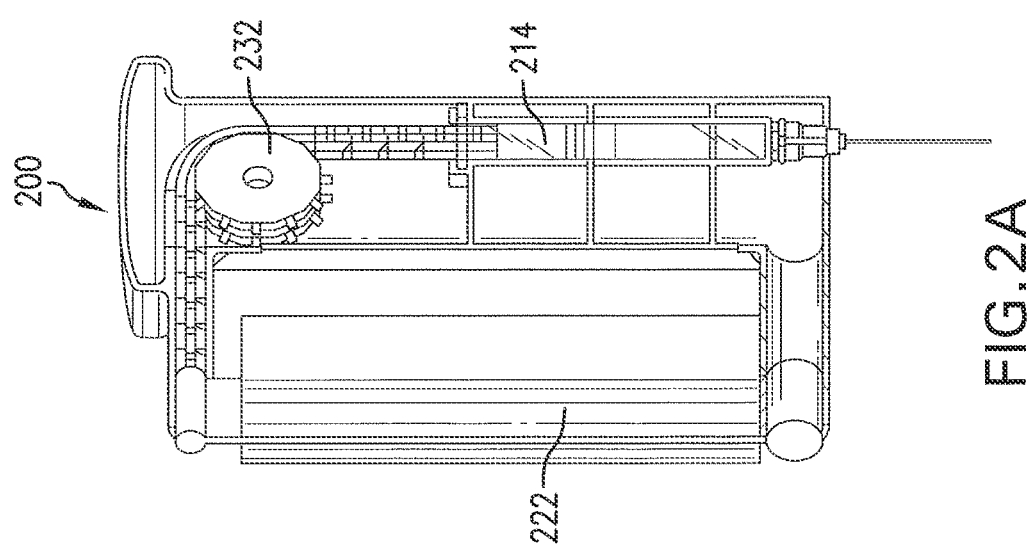

MANUALLY-ACTUATED INJECTION DEVICE FOR HIGH-VISCOSITY DRUGS

This application is a continuation of, and claims the priority benefit of, U.S. non-provisional application Ser. No. 16/462,354, filed on May 20, 2019, which is a U.S. National Stage Entry of PCT International Application No. PCT/US2017/062560, filed on Nov. 20, 2017, which claims the priority benefit of U.S. provisional application No. 62/424,746, filed Nov. 21, 2016, each of which is hereby incorporated by reference in their entirety.

FIELD OF INVENTION

In general, the present disclosure relates to injection devices for use with pharmaceuticals, i.e., hypodermic injection devices. More specifically, the disclosure relates to injection devices for injecting high-viscosity pharmaceuticals into the body of a human patient.

BACKGROUND OF THE INVENTION

As the pharmaceutically active molecules in certain medications (e.g., biologics) become larger and more complex, the medications tend to be more viscous. For example, while many common injectable drugs have viscosities on the order of 2 or 3 cp (centipoises), it is not unheard of for certain injectable drugs to have viscosities on the order of 50 cp or 60 cp. Understandably, as the viscosity of the injectable drug increases, so, too, will the difficulty in injecting the drug. Accordingly, it can become more difficult to ensure that a complete dose is delivered with each injection. Additionally, difficulty with self-administration can lead to non-compliance and therefore diminished treatment efficacy.

Additionally, even where a prescribed drug does not necessarily have increased viscosity, as patients age or otherwise become frail, they tend to have more difficulty self-administering injectable medications. This may be attributable to loss of the manual dexterity required to hold and steady a conventional syringe while depressing the syringe plunger, as well as loss of the finger/thumb strength required to depress the plunger.

In this regard, it is a generally accepted "rule-of-thumb" in the industry that, at least when a patient is self-administering an injection, the limit for patient comfort during the injection procedure is about ten seconds. After ten seconds, most patients start to get uncomfortable, squirm, and may even remove the syringe before a full dose of medication has been delivered. However, given the cost of certain medications, many medical-cost-reimbursing organizations (e.g., insurance companies) want to be certain that full doses are delivered and patients comply with their dosing regimens.

Therefore, as one way to ensure delivery of a full dose of (high-viscosity) medication within the ten-second "window" of comfort, motor-driven syringes have been developed. In addition to the motor itself, motor-driven syringes include batteries, on-board electronics, and associated circuitry to control operation of the motor as well as to track patient compliance with the prescribed dosing regimen. However, such motorized injection devices can be substantially more expensive than conventional syringes, and the higher cost is frequently seen as a waste of medical dollars given that such devices are discarded after a single use.

SUMMARY OF THE INVENTION

Embodiments of the present invention provide hypodermic injection devices that are well suited for injecting highly viscous medications in a rapid, patient-friendly manner, which enhances patient compliance with prescribed dosing regimens at less cost as compared to motor-driven or other "electronic" syringes. The disclosed hypodermic injection devices take advantage of the greater force that can be generated—up to six times as much force—by "gripping" and squeezing the injection device (i.e., by closing four fingers toward the palm or heel of the hand), as compared to the force that can be generated by using the thumb to press downward on the plunger of a conventional syringe (which is held between the index and middle fingers of the drug-injecting hand while the thumb depresses the plunger). The gripping and squeezing motion associated with using embodiments of the present invention facilitates injecting medications with generally higher viscosities.

Thus, in one aspect, the invention features an injection device for injecting medication into the body of a patient. The injection device includes a housing with a medication-receiving chamber disposed therein, with the medication-receiving chamber having a medication discharge port; a push member disposed within the housing and arranged to move in a direction that causes medication contained within the medication-receiving chamber to be pressurized; a grip member moveably connected to the housing; and a force-transfer mechanism operatively coupling the grip member and the push member.

The medication-receiving chamber and the medication discharge port are configured and arranged such that when the housing is held across the palm of a medication-administering person's hand with the grip member positioned to be engaged by the administering person's non-thumb fingers in a gripping and squeezing motion, pressurization of medication within the medication-receiving chamber will cause the medication to be discharged, via the medication discharge port, in a direction toward the outer, blade edge of the device-holding hand. Furthermore, the grip member is connected to the housing in a manner such that squeezing the grip member via the gripping and squeezing motion causes at least a portion of the grip member to move toward the housing. Further still, the force-transfer mechanism is arranged to transfer movement of the grip member, caused by squeezing the grip member with a first, net amount of force, to the push member so as to pressurize medication contained within the medication-receiving chamber with a second amount of force and cause the medication to be discharged via the medication discharge port.

Ideally, the force-transfer mechanism may be configured to amplify the amount of force applied to the grip member, so that a greater amount of force is applied to the push member to pressurize and discharge the medication than is applied to the grip member. This may be accomplished by providing the force-transfer mechanism with multiple (i.e., differential) moment arms, or by arranging the force-transfer mechanism so that multiple moment arms are created during operation of the device.

Furthermore, components within various embodiments of a medication-injecting device according to the invention can take a variety of different configurations. For example, the injection device may include a pair of guide rails extending laterally from the housing and parallel to each other, with the grip member extending between the guide rails. In such an embodiment, the grip member moves translationally toward the housing, along the guide rails, when it is squeezed. Alternatively, the grip member could be pivotally attached to the housing. In such pivoting-grip-member embodiments, the grip member could be attached to the housing at an end of the grip member, in which case the entire body of the grip member pivots toward the housing when the grip member is being squeezed. Such a configuration of the grip member works well when forces are transferred in compression.

Alternatively, e.g., in the case of dogleg-shaped grip members, the grip member could be pivotally attached to the housing at an attachment point located at a juncture between the two legs. Depending on the orientation of the dogleg-shaped grip member, squeezing one of the legs of the grip member could cause the other leg of the grip member to rotate in a downward direction, which pushes on the push member (i.e., transfers force in compression) in an injection-force-applying direction. Or, the configuration could be such that squeezing one of the two legs such that it pivots toward the housing causes the other of the two legs to pivot away from the housing. This configuration is advantageous in embodiments where forces are transferred, at least partially, in tension.

The force-transfer mechanism may include continuous or essentially continuous components, such as flexible tapes or chains (including tapes and chains that have sufficient rigidity to transfer force in compression). Alternatively, the force-transfer mechanism could include multiple discrete (i.e., separately identifiable) components such as pinion gears or sector pinion gears, rack gears, and/or rigid linkage members. Ideally, the force-transfer mechanism includes at least one component configured for lost motion, e.g., via a ratcheting mechanism or a slotted-gear mechanism, which facilitates configuring the injection device to prevent reuse.

In a related aspect, the invention features a method for injecting medication into a patient. The method includes grasping an injection device in a medication-administering hand; inserting the hypodermic needle portion of the injection device into the patient's body; and causing the medication to be discharged from the injection device by squeezing the injection device (i.e., by closing the non-thumb-fingers of the medication-administering hand toward the palm and/or heel of the medication-administering hand).

As noted above, this method of gripping and squeezing the injection device with the non-thumb fingers facilitates injecting medications with generally higher viscosities. For example, the method can be used in certain embodiments to inject medications with a viscosity of up to about 50 centipoise or more, and full dose of the medication can be discharged from the injection device within the patient-comfort "window" of about ten seconds or less. Furthermore, this method of injecting a medication facilitates resting the outer, blade edge of the medication-administering hand against the patient's skin while the medication is being injected, to stabilize the injection device. This, too, improves the injection experience.

BRIEF DESCRIPTION OF THE DRAWINGS

These and other features of the invention will become clearer from the detailed description below as well as the drawings, in which:

FIGS. 1A, 1B, and 1C are schematic perspective views illustrating a first embodiment of an injection device according to the invention, wherein FIG. 1B shows internal components thereof, and FIG. 1C shows the injection device of FIGS. 1A and 1B being held within a user's hand;

FIG. 2A is a schematic perspective view illustrating internal components of a second embodiment of an injection device according to the invention;

FIG. 2B is an enlarged view of certain components of the device shown in FIG. 2A;

DETAILED DESCRIPTION OF EMBODIMENTS OF THE INVENTION

Figure 3A:
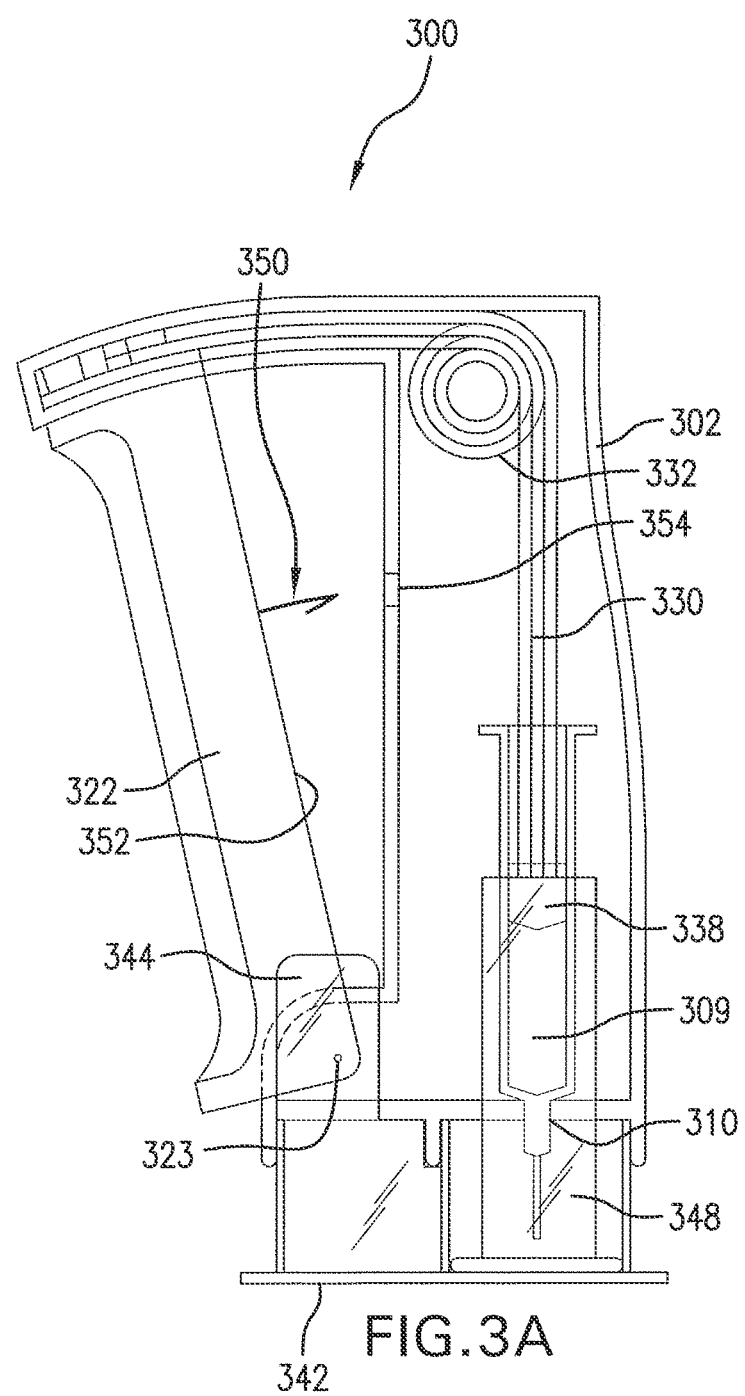
FIGS. 3A, 3B, and 3C are schematic side views illustrating internal components of a third embodiment of an injection device according to the invention as the injection device is used to inject medication into a patient.

A first embodiment of an injection device 100 according to the invention is illustrated in FIGS. 1A, 1B, and 1C. The injection device 100 includes a generally elongated housing 102, which is formed, e.g., by injection molding, from medical-grade material such as plastic. Suitably, the housing 102 is formed from two symmetric halves, which can be secured together, e.g., by barbed pins, ultrasonic welding, or other suitable means, after various internal components—including, in most embodiments, a prefilled hypodermic syringe assembly 104—have been assembled into the housing 102.

A medication-receiving space or chamber 106, which is configured to receive a dose of medication therein, is formed within the housing 102. For example, the chamber 106 may be formed by contoured sidewalls 108, which surround or otherwise engage and securely hold the syringe portion 109 of the syringe assembly 104 when the halves of the housing 102 are assembled together. Although the term "chamber" is used herein, for embodiments in which a prefilled syringe assembly 104 is housed within the injection device 100, it is not necessary or implied that the chamber 106 will be sealed. Rather, the chamber 106 is simply that portion of the injection device 100 where the dose of medication will be housed when the injection device 100 is "loaded" and ready to be used to administer the dose of medication.

The chamber 106 also has a medication discharge port 110 located at an end thereof. For example, as illustrated in FIGS. 1A, 1B, and 1C, the discharge port 110 may simply be an aperture through which the hypodermic needle portion 112 of the syringe assembly 104 protrudes such that medication being injected into the patient via the hypodermic needle 112 will exit the chamber 106 by passing through the discharge port 110.

Further still, the injection device 100 has a push member 114, which pressurizes and therefore forces medication out of the device 100. For example, in the case of embodiments using a prefilled hypodermic syringe assembly 104, the push member suitably may be the plunger of the syringe assembly 104, which plunger includes a plunger rod 116 and a piston 118 at the end of the plunger rod 116. As will be understood by those skilled in the art, the piston 118 is suitably formed from elastomeric material such as silicone or rubber and bears against the walls of the syringe portion 109 to seal the medication within the syringe. When force is applied to the plunger in a direction toward the hypodermic needle portion 112, the medication is pressurized within the syringe portion 109, which causes the medication to flow out of the syringe portion 109 through the hypodermic needle portion 112.

The housing 102 further includes a grip-supporting portion 120 that is configured to support a grip member 122 in generally spaced, laterally moveable relationship relative to the portion of the housing that holds the medication. For example, as illustrated in FIGS. 1A, 1B, and 1C, the grip-supporting portion includes a pair of hollow, upper and lower slotted guide rails 124a and 124b that extend perpendicularly from the portion of the housing 102 with the medication-receiving chamber 106. The grip member 122 includes a central, finger-engaging body portion 126 and a somewhat bulbous guide lug 128a, 128b at the upper and lower end of the body portion 126, respectively, with the guide lugs 128a, 128b being connected to the body portion 126 of the grip member 122 by means of web portions 129a, 129b, respectively. As illustrated in FIG. 1B, the guide lugs 128a, 128b fit within the guide rails 124a, 124b, respectively, and are shaped and sized to conform generally to the interior surfaces of the guide rails 124a, 124b. The connecting web portions 129a, 129b extend through corresponding slots (not labelled) that are formed in the lower and upper surfaces of the upper and lower guide rails 124a, 124b, respectively, when the halves of the housing 102 are assembled together. This configuration permits the grip member 122 to slide laterally relative to the housing 102 and toward the portion of the housing that contains the medication. End caps (not illustrated) may be provided at the ends of the guide rails 124a, 124b to restrain the grip member 122 within the guide rails 124a, 124, or other means (not illustrated) such as a tether extending between the grip member 102 and the opposing portion of the housing 102 could also be used.

As further illustrated in the figures, the injection device includes a force transmission mechanism that couples the grip member 122 to the push member 114. For example, in the embodiment illustrated in FIGS. 1A, 1B, and 1C, the force transmission mechanism includes a semi-rigid tape member 130 that is securely attached (e.g., by pins, rivets, or sonic welding) to the flat, upper surface (not labelled) of the upper guide lug 128a at one end, and to the push member 114 at its opposite end. A pinion gear 132, around which the tape member 130 passes, has axle-forming pins (not illustrated) extending from either side of it, and the axle-forming pins fit within receptacles (not illustrated) formed in the two halves of the housing 102 to support the pinion gear 132 and allow it to rotate. The tape member 130 suitably has a number of holes 134 extending through it to enhance its flexibility, so that it can wrap smoothly around the pinion gear 132, and the holes 134 engage with pins or teeth 136 extending from the periphery of the pinion gear 132 to keep the tape member 130 properly aligned within the injection device 102. Furthermore, although the tape member 130 has enough rigidity to allow it to transmit force to the push member 114 in compression (i.e., by pushing against the push member 114), it may be preferable for the tape member to be restrained within a slot (not illustrated) that is formed within the housing to prevent the tape member 130 from buckling or flexing transverse to the direction of force transmission.

With this configuration, the injection device 100 can be used as follows. As shown in FIG. 1C, the injection device 100 is held with the portion of the housing 102 that contains the medication extending across the palm of the injection-administering hand 138, i.e., in a direction generally transverse to the direction in which the non-thumb fingers (index, middle, ring, and pinky) extend, with the discharge port 110 located at or slightly outward relative to the outer, blade edge 140 of the medication-administering hand. The non-thumb fingers can then be curled into light engagement with the grip member 122 to hold the injection device 100, and the hypodermic needle 112 is inserted into the patient's body at the medication-administration site. Once the needle is inserted into the body, the non-thumb fingers are further curled to squeeze the grip member 122 toward the medication-containing portion of the housing 102 with a gripping motion. (In human-factors engineering, this motion is referred to as a "power grip" motion.) The force transmission mechanism (e.g., the tape member 130) transfers the gripping force applied to the grip member 122 by the fingers—and hence the resulting motion of the grip member 122 relative to the housing 102—to the push member (e.g., the plunger rod 116 and the piston 118). This pressurizes the dose of medication contained within the syringe assembly 104, thereby causing the medication to flow along the hypodermic needle 112, through the discharge port 110, and into the patient.

Notably, this configuration provides at least two distinct advantages. First, on average, an adult human can generate up to six times as much force with a gripping and squeezing motion as can be generated simply by pushing with the thumb (as per the conventional mode of delivering an injection). Therefore, with a configuration as shown in FIGS. 1A, 1B, and 1C, where there is a 1:1 relationship between the amount of force applied to the grip member 122 and the amount of force applied to the push member 114, six times more pressurizing force can be applied to the medication in the syringe than would be the case of a conventional mode of administration. Given the increase in pressurizing force that can be generated using an injection device as per the invention, the hypodermic needle 112 does not need to have as large a bore to convey and deliver higher-viscosity medications. Thus, higher-viscosity medications may be injected using smaller and thinner hypodermic needles. This is an advantage as smaller, thinner needles are less intimidating and more comfortable for patients when higher-viscosity medications need to be administered. (An injection device in accordance with the invention could also be used with medications that have more conventional, lower-range viscosities.) Although it may still be the case that somewhat-larger-bore needles need to be used to avoid friction-induced, molecule-destroying shear forces being generated within the medication as it passes through the hypodermic needle, the increase in needle bore should not need to be as great as otherwise would be the case if only thumb-pressure were being used to deliver the medication.

Second, given the location of the discharge port 110 near the blade edge 140 of the medication-administering hand 138, the blade edge of the medication-administering hand 138 can be rested against the patient's body to stabilize the injection device 100 as the injection is being administered. This, too, increases patient comfort, and should be particularly beneficial when a patient self-administers the medication.

A second, similar embodiment of an injection device 200 according to the invention is illustrated in FIGS. 2A and 2B. Given the similarity of the embodiment 200 to the embodiment 100, the description of the second embodiment 200 will be limited to just the primary point of difference between the two, which lies in the force transmission mechanism.

To increase its flexibility and help the force transmission mechanism curve around the pinion gear 232, the force transmission mechanism in the second embodiment 200 consists of a segmented, compressive-force-transmitting drive chain 230. Suitably, each of the links 231 in the drive chain 230 has a plus sign-shaped (+) cross-section, which helps stiffen the chain 230 in its longitudinal direction when the links 231 are aligned with each other so as to better transmit compressive forces. As illustrated, the downwardly extending ribs or flanges 233 of the links 231—i.e., the ribs or flanges that will be located on the inside of the curve as the drive chain 230 wraps around the pinion gear 232—fit within a groove 237 that extends around the periphery of the pinion gear 232, and holes or apertures 234 in the laterally extending ribs or flanges 235 engage with pins or teeth 236 extending from the peripheral surface of the pinion gear 232 on either side of the groove 237 to help retain the drive chain 230 in proper position. Furthermore, sequential links 231 in the drive chain 230 pivotally or flexibly engage with each other by means of a rounded, transversely extending rib 239 at one end of each link, which rib 239 fits within a correspondingly shaped receiving slot 241 that is formed at the opposite end of each link 241. Construction and operation of the embodiment 200—which, like the embodiment 100, has a 1:1 force-transmission ratio between the grip member 222 and the push member 214—are otherwise the same as in the embodiment 100.

In the embodiments 100 and 200 of an injection device according to the invention, the grip member 122 or 222 is arranged generally parallel to, and it moves linearly and laterally (i.e., translationally) toward, the portion of the housing containing the medication. For most people, however, the distance between the heel of the palm of the hand and the first knuckle of each finger (i.e., the metacarpophalangeal joint) is somewhat larger for the index and middle fingers than it is for the ring and pinky fingers. Therefore, to conform somewhat more closely to the anatomy of a human hand, it may be preferable for the grip member of the injection device to be angled relative to the housing.

Figure 3B:
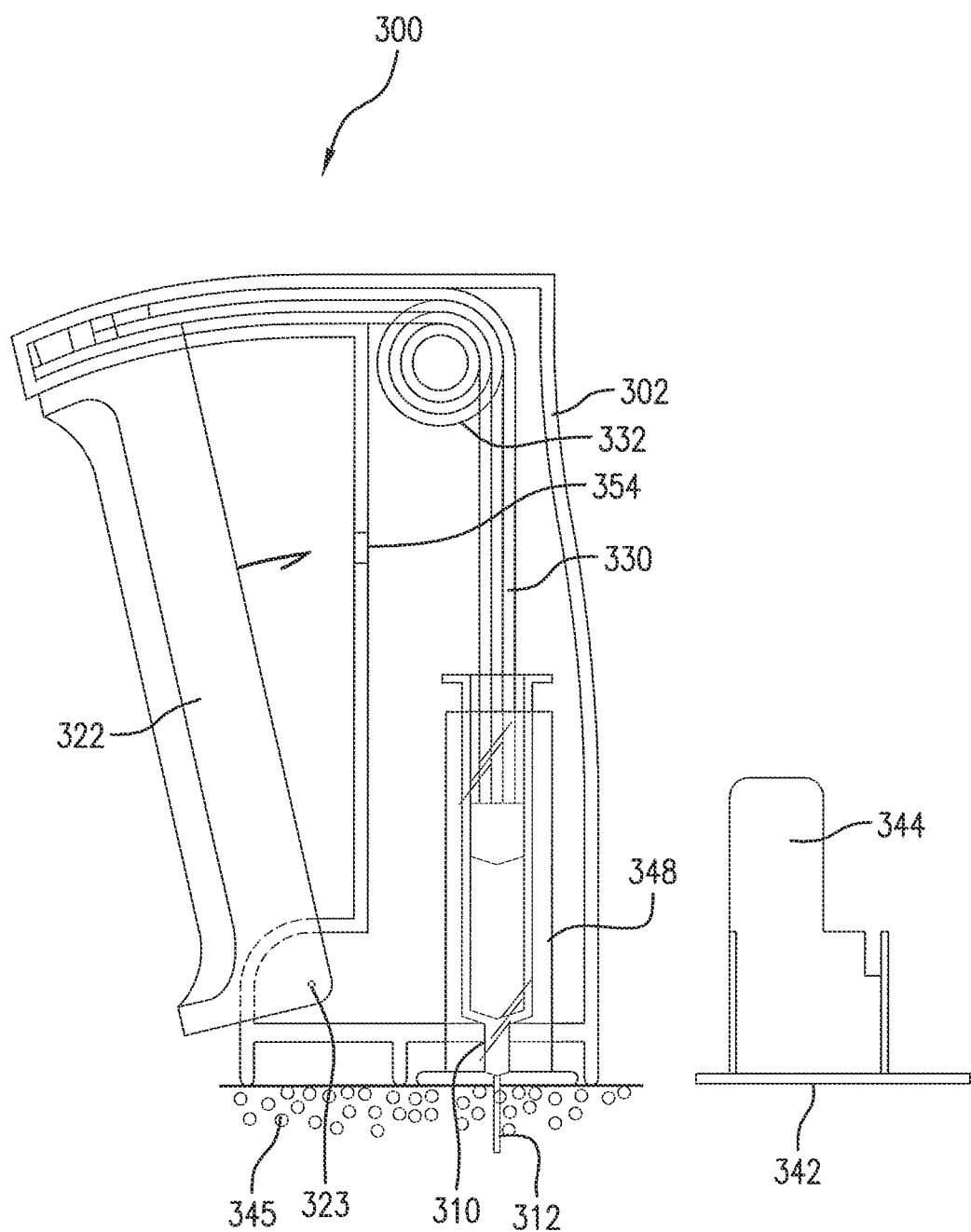
Figure 3C:
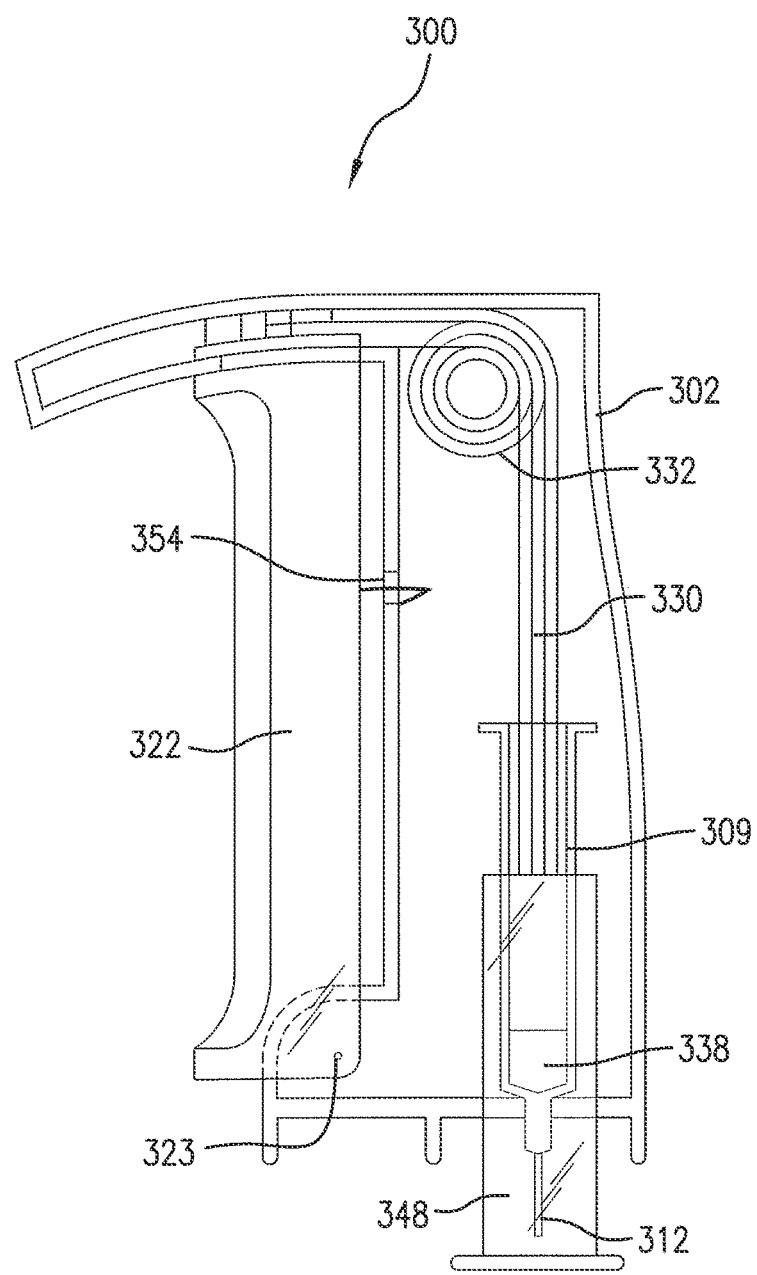

For example, as illustrated in FIGS. 3A, 3B, and 3C, in an embodiment 300 of an injection device according to the invention, the grip member 322 is pivotally connected to the housing 302 at a pivot point 323 that is generally near the lower, injection end of the injection device 300. This configuration allows the grip member 322 to pivot toward the portion of the housing 302 containing the medication as the grip member 322 is gripped and squeezed, which may be more comfortable for some users. Furthermore, a constant-force, wound-coil spring (not illustrated) may be connected to the pinion gear 332 to reduce sensed resistance and enhance ease of use. Medication-injecting operation of the injection device 300, which utilizes a force-transmitting chain 330 that is the same as or similar to that used in the injection device 200 as its force transmission mechanism, is similar to the same as operation of the injection device 200.

Thus, as further illustrated in FIGS. 3A, 3B, and 3C, the injection device 300 is provided with a closure cap 342, which fits over the injection end of the injection device 300 to guard against accidental needle-sticks. Furthermore, the closure cap 342 may be configured to prevent actuation of the injection device 300 while the cap 342 is still in place. For example, as illustrated in FIG. 3A, tab or tabs 344 protruding from the closure cap 342 extend into a position that blocks movement of the grip member 322 toward the portion of the housing containing the medication.

To use the injection device 300, the closure cap 342 is removed (FIG. 3B), and the injection device 300 is pressed against the patient's body 345. As the injection device 300 is advanced toward the patient's body 345 and the hypodermic needle 312 penetrates the body 345, a spring-biased needle guard 348, which shrouds the needle 312, is depressed inwardly into the interior of the housing 302. The grip member 322 is then squeezed, which causes it to pivot toward the medication-containing portion of the housing 302. Movement of the grip member 322 toward the housing drives the piston 338 downwardly, which pressurizes medication in the syringe 309 to discharge it from the device 300, along the hypodermic needle 312 and through the discharge port 310.

Suitably, the injection device 300 further has a locking mechanism, which holds the grip member 322 in the fully actuated position once the medication contained in the injection device 300 has been discharged. For example, a flexible barbed finger 350 may be provided on an inner surface 352 of the grip member 322, extending toward the medication-containing portion of the housing 302. As the grip member 322 pivots toward its fully actuated position (FIG. 3C), the end of the barbed finger 350 enters a slot 354 formed in the side of the housing 302, with the finger 350 flexing as it does so. Once the injection device 300 has been discharged, the barbed end of the barbed finger 350 holds the grip member 322 in the fully actuated position so that the device cannot be used to administer another injection.

After the medication has been injected, the hypodermic needle 312 is withdrawn from the patient's skin 345 (FIG. 3C). The spring-biased needle guard 348 then extends automatically back out of the housing to shroud the needle 312 and help prevent accidental needle sticks.

In the embodiments 100, 200, and 300 described so far, assuming there is no coil spring to apply a turn-assisting force to the pinion gear, the amount of force applied to the push member will be essentially the same as the net amount of force applied to the grip member along its length, since the force transmission mechanism (tape 130 or chain 230, 330) is essentially a unitary member that extends directly from the grip member to the push member. Thus, in these embodiments, there is a 1:1 ratio (or essentially a 1:1 ratio) of force applied to the grip member to force applied to the push member.

Advantageously, however, an injection device as per the invention may utilize force-amplifying components as part of the force-transmission mechanism. For example, as illustrated in FIG. 4, the force transmission mechanism in another embodiment (not illustrated in its entirety) could be discontinuous (in the sense that the force-transmission pathway extends through multiple components), with a force-amplifying component that couples the various subcomponents to each other to establish the entire force-transmission pathway.

Figure 4:
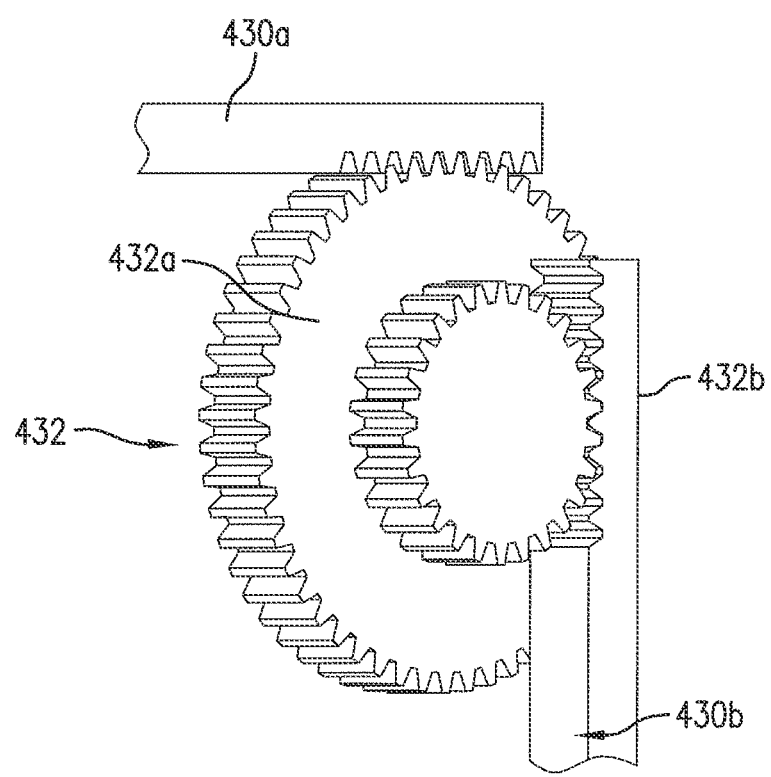
FIG. 4 is a schematic perspective view of internal components used in a fourth embodiment of an injection device according to the invention.

More particularly, the force transmission mechanism illustrated in FIG. 4 is comprised of a rack-and-pinion mechanism, with the grip member (not illustrated) applying a turning force (i.e., a torque) to teeth along the outer periphery of the larger-diameter portion 432a of staged pinion gear 432 via grip rack 430a. On the other hand, plunger rack 430b, which depresses the plunger assembly (not illustrated) of a hypodermic syringe, engages with teeth along the outer periphery of the smaller-diameter portion 432b of the staged pinion gear 432. Given the shorter moment arm of the plunger rack 430b relative to the axis of the staged pinion gear 432 as compared to the moment arm of the grip rack 430a, torque balance will cause the force applied to the plunger rack 430b, and hence to the plunger assembly of the syringe, to be larger than the net force applied to the grip member. In other words, the plunger rack 430b will apply to the push member a pressurizing force that is a multiple of the net force applied to the grip member, with the multiplying factor being greater than 1. Such a feature further enhances the ease with which high-viscosity medications can be injected with an injection device according to the invention.

Figure 5A:
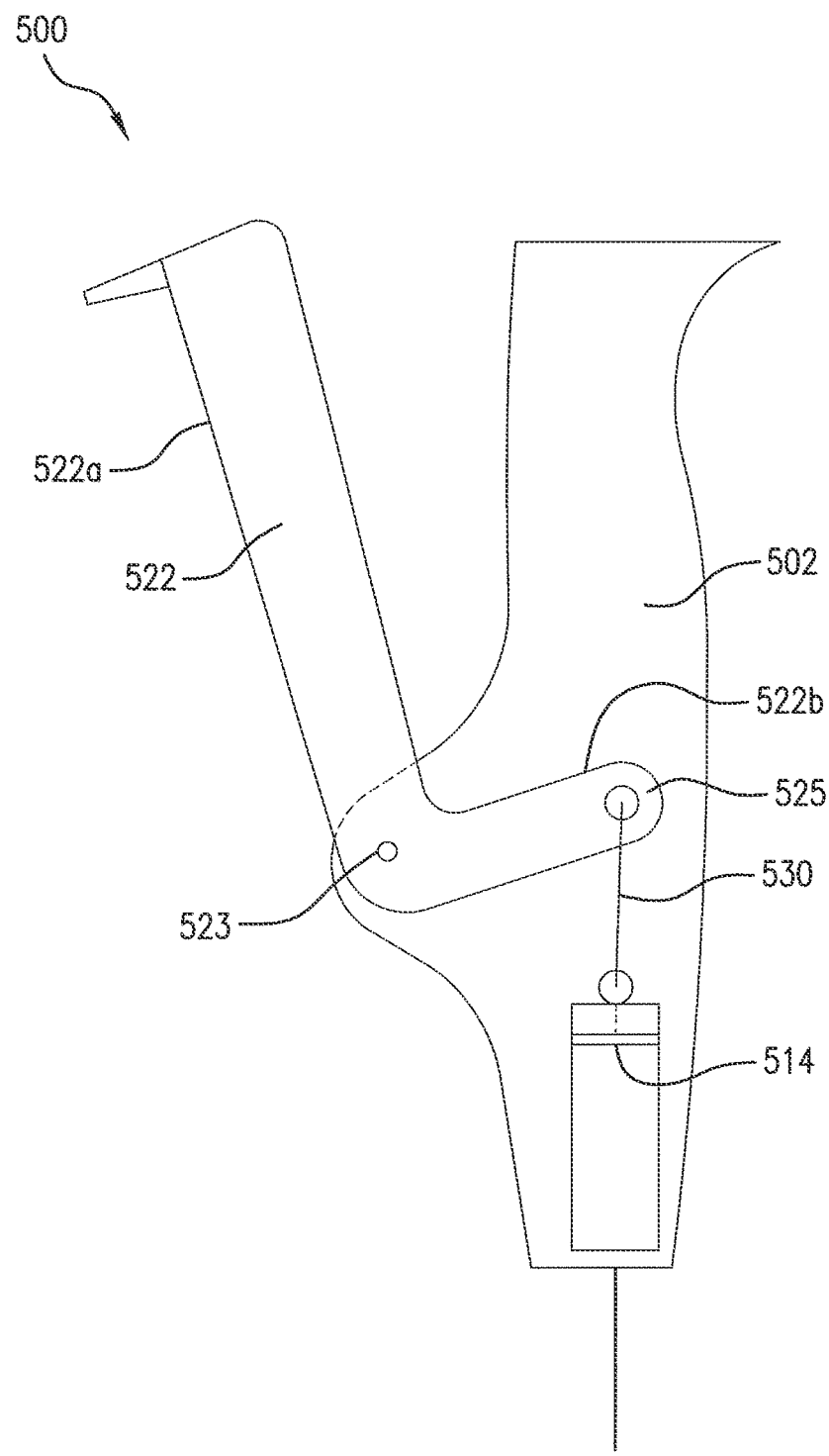
FIGS. 5A and 5B are schematic side views illustrating internal components of a fifth embodiment of an injection device according to the invention as the injection device is used to inject medication into a patient.
Figure 5B:
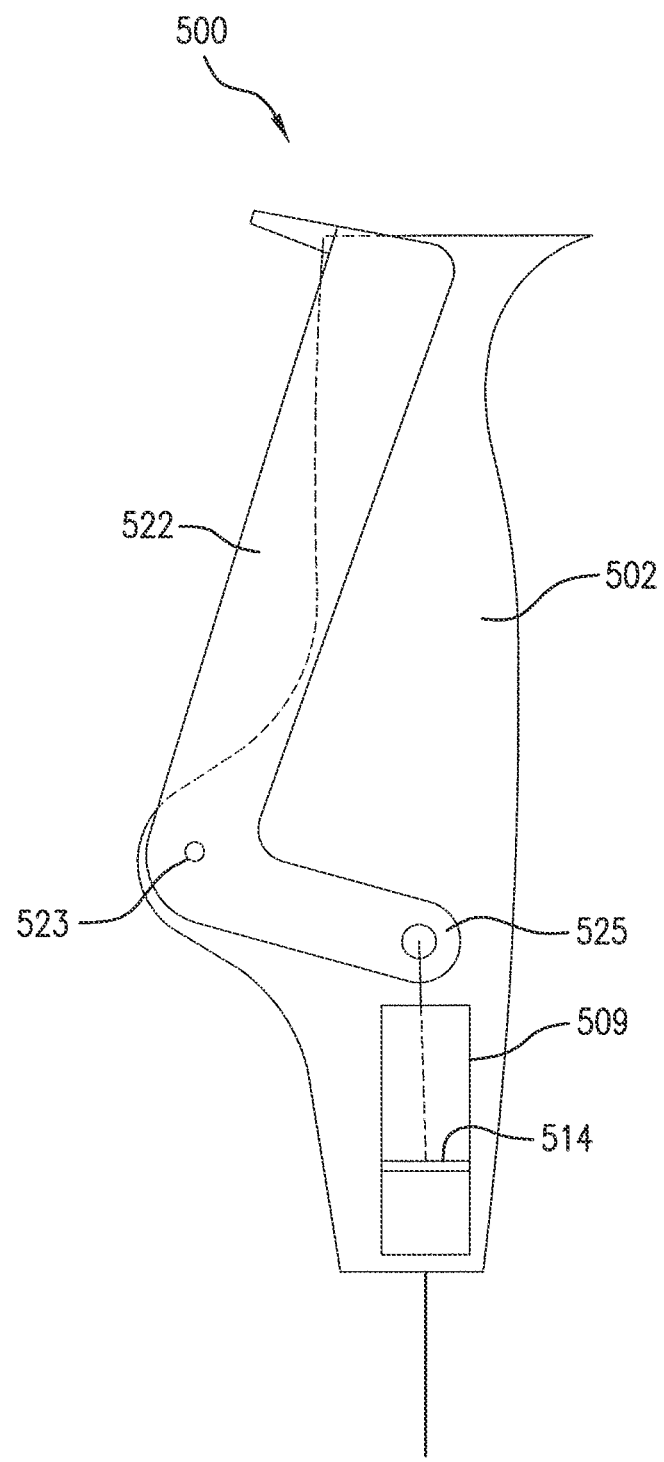

Another force-amplifying embodiment 500 of an injection device according to the invention is illustrated in FIGS. 5A and 5B, which are generally schematic in nature. Like the above-described embodiment that uses a staged pinion gear with two different moment arms to increase applied force, the embodiment 500 also makes use of two different moment arms, provided by a bell crank, to increase the injecting force that is applied to the medication. In particular, the grip member 522 in the embodiment 500 is generally L-shaped, with a pivot axis 523—by means of which the grip member 522 is pivotally attached to the housing 502—that is located at the junction between the long, "vertical" leg 522a of the L and the short, "horizontal" leg 522b of the L. A force-transfer linkage member 530 is pivotally connected to the free end 525 of the short leg 522b of the L and provides pressurizing force to medication contained within the syringe 509, e.g., via push member (piston) 514. Because the force applied to the medication via the force-transfer linkage member 530 acts along a line of action that is closer to the pivot axis 523 (perpendicular distance) than the center of gripping force applied to the leg 522a is, torque balance will cause the amount of force applied to the medication to be greater than the amount of gripping force applied to the grip member by the administering person's hand. Thus, the embodiment 500 illustrated in FIGS. 5A and 5B also has a force-amplifying effect (multiplying factor greater than 1). Furthermore, the value of the multiplying factor can be tailored by changing the relative values of the respective moment arms and/or the angle between the two legs 522a and 522b of the grip member 522.

Figure 6A:
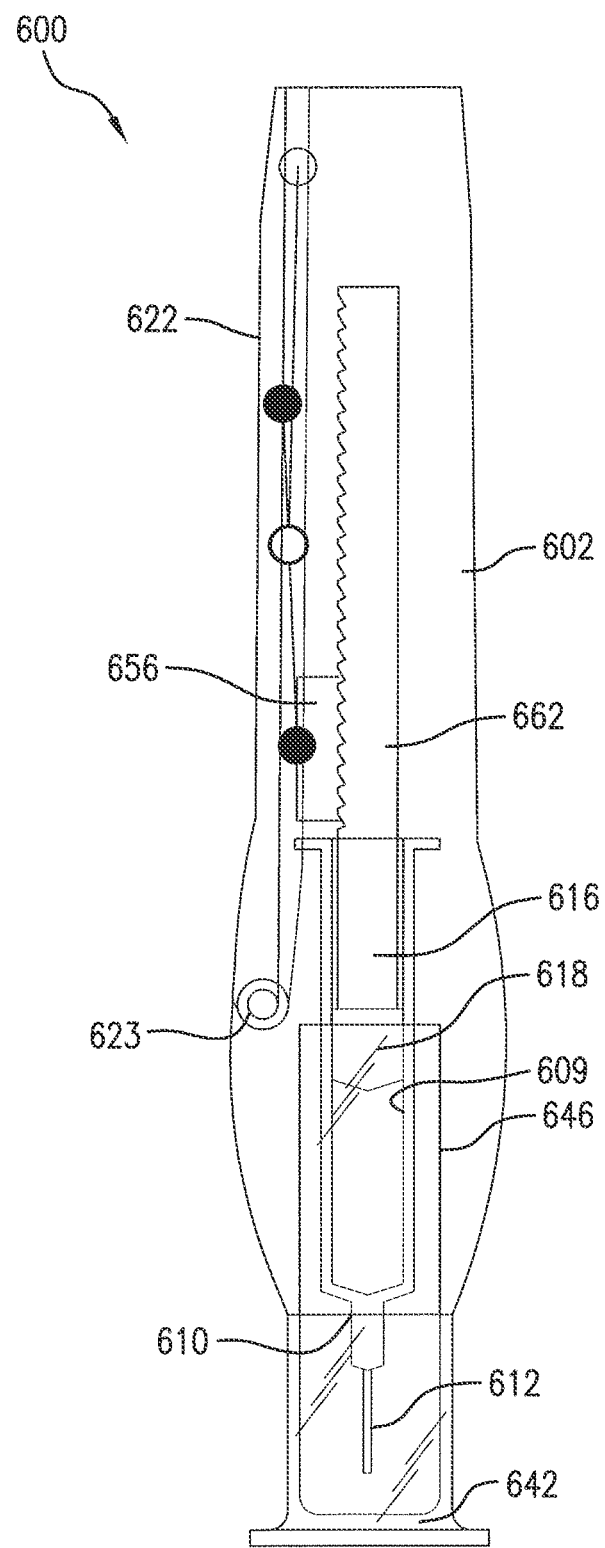
FIGS. 6A, 6B, and 6C are schematic side views illustrating internal components of a sixth embodiment of an injection device according to the invention as the injection device is used to inject medication into a patient.
Figure 6B:
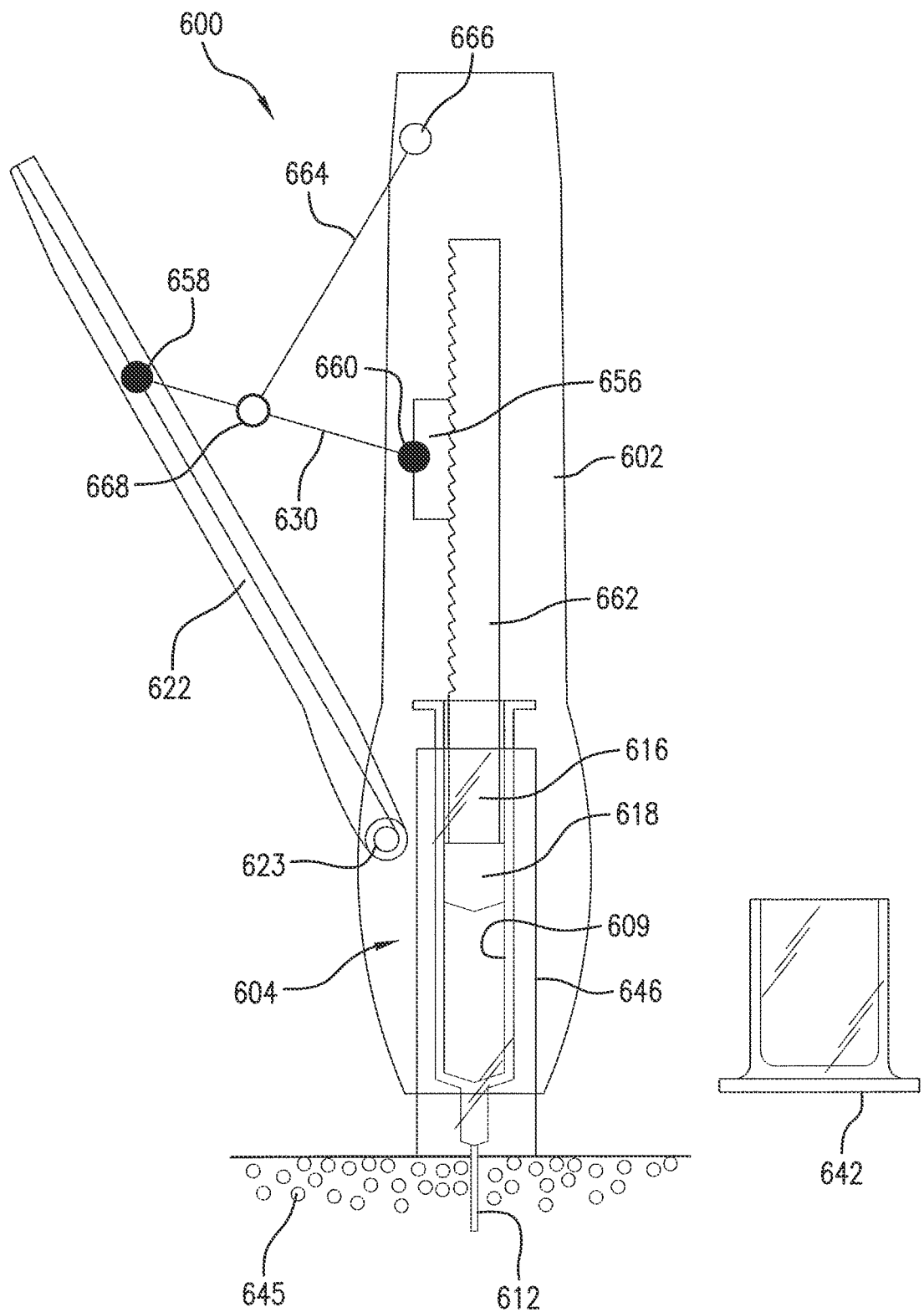
Figure 6C:
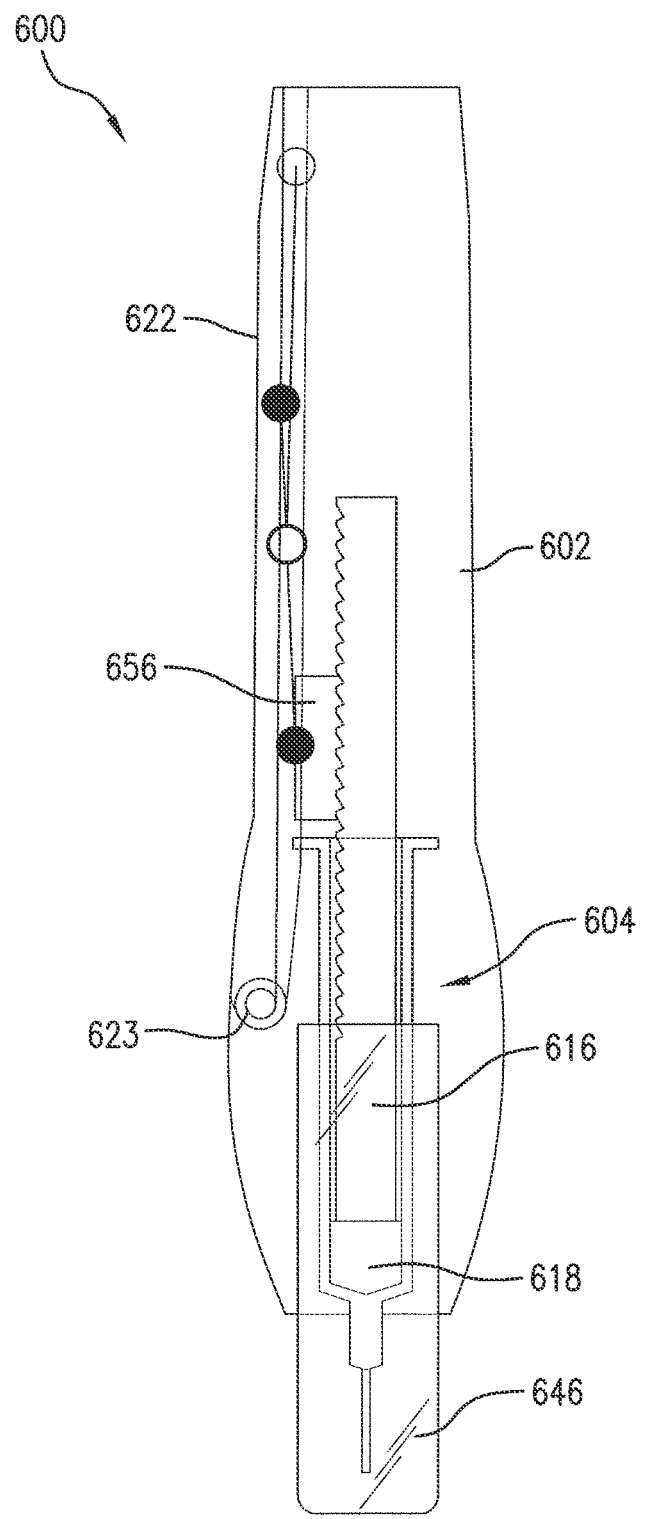

In the embodiment 600 illustrated in FIGS. 6A, 6B, and 6C, a sliding ratchet block 656 is used to transfer pressurizing force to the push member, and hence to the medication contained within the injection device, in a single-use configuration. More particularly, the embodiment 600 has a grip member 622, which is pivotally connected via pivot axis 623 at its lower end to housing 602. As shown in FIG. 6A, in a packaged configuration of the injection device 600, the grip member 622 lies flush against the housing 602 of the injection device, and the ratchet block 656 is located at a forward position thereof. Additionally, a closure cap 642 is suitably provided at a front end of the device to prevent accidental needle sticks. Suitably, the closure cap 642 fits over the end of spring-biased, retractable protective sleeve 646, which extends out of the housing 602 and surrounds the hypodermic needle 612.

When the injection device 600 is to be used, the closure cap 642 is removed, and the grip member 622 is pivoted away from the housing 602, to the position shown in FIG. 6B. As the grip member 622 pivots away from the housing 602, rigid linkage member 630, which is pivotally connected to the grip member 622 at pivot connection 658 and to the ratchet block 656 at pivot connection 660, pulls the ratchet block 656 backward, away from the discharge end of the injection device 600. As the ratchet block 656 moves backward, its ratchet teeth, which cooperate with corresponding ratchet teeth formed along the side of ratchet rod 662, slip past the ratchet teeth of the ratchet rod 662. Suitably, biasing means such as a spring, not illustrated, hold the ratchet block 656 in engagement with the ratchet rod 662 as the ratchet block 656 slides past the ratchet rod 662. Additionally, restraint linkage member 664, which is pivotally connected to the housing 602 at pivot axis 666 and slidably connected to rigid linkage member 630 at connection point 668, prevents the grip member 622 from being rotated too far outwardly from the housing 602, which could otherwise cause the ratchet block 656 to move so far backward that it loses its ability to push the ratchet rod 662 forward.

As shown in FIG. 6B, the hypodermic needle 612 is then inserted into the patient's body 645 at the injection site (which insertion action depresses the protective sleeve 646 into the housing 602), and the grip member 622 is squeezed to cause it to pivot back toward the housing 602. As the grip member 622 pivots toward the housing 602, rigid linkage member 630 applies a forward-acting force to the ratchet block 656; because the teeth of the ratchet block 656 and the ratchet rod 662 are configured to prevent relative movement between the ratchet block 656 and the ratchet rod 662 when the ratchet block is moving forwardly, the ratchet block 656 forces the plunger 616 and piston 618 of the syringe assembly 604 forward, thereby causing medication contained within the syringe to be injected into the patient's body 645. In this embodiment 600, force amplification will vary generally sinusoidally with the position of the grip member 622, as angles between the linkage member 630, the grip member 622, and the ratchet block 656 vary.

After all of the medication has been injected (FIG. 6C), the hypodermic needle 612 is withdrawn from the patient's body 645, and the protective sleeve 646 extends outwardly from the housing 602 to surround the needle 612 and help prevent accidental needle-sticks.

Advantageously, in the embodiment 600, the ratchet block 656—which is a unidirectional, lost-motion element in the sense that it transfers pressurizing/injecting force to the medication in one direction but it slips past the force-transmitting member (the ratchet rod 662) in the opposite direction—provides the injection device 600 with an "open-to-cock, close-to-discharge, single-use" configuration. This feature increases the user's confidence that he or she is using the device in the correct manner and improves safety by preventing reuse of the device. In other words, as illustrated in FIG. 6A, the injection device 600 can be provided to the patient in a compact, "tidy," primed configuration. The device 600 is readied for use (i.e., "cocked") by pivoting the grip member 622 away from the housing 602, to the position illustrated in FIG. 6B. And once the grip member 622 has been pivoted back toward the housing 602 to dispense the medication as illustrated in FIG. 6C, the ratchet rod 662 and piston 618 will remain in their forward, advanced positions because pivoting the grip member 622 back away from the housing 602 once again will only cause the ratchet block 656 to slip backward past the ratchet rod 662. Firm engagement between the piston 618 and the inside walls of the syringe 609, which holds the piston in its forward position; a shallow angle of the teeth on the ratchet block 656 and the ratchet rod 662; and use of low-friction materials for the ratchet block 656 and the ratchet rod 662 to facilitate relative slipping help ensure that the ratchet rod 662 is not retracted (pulled backward) by the ratchet block 656 if the grip member 622 is pivoted outwardly once again.

This relative slipping motion of the ratchet members prevents the injection device 600 from being reused by drawing substances back into the syringe 104 via the needle 612. Additionally, once the ratchet rod 662 and piston 618 have reached (and remain in) their most-forward position, it will be impossible to drive them farther forward. Therefore, if the grip member 622 is pivoted outwardly once again after the medication has been discharged, which outward-pivoting motion will draw the ratchet block 656 back toward the rear end of the ratchet rod 662, engagement of the ratchet block teeth against the ratchet rod teeth—and the inability of the ratchet rod and piston to move farther forward—will effectively lock the grip member 622 in its re-extended position. This feature further prevents reuse of the injection device 600.

Two somewhat-similar open-to-cock, close-to-discharge embodiments 700 and 800—both of which use a sectored pinion gear and rack to transmit force from the grip member to the push member—are illustrated in FIGS. 7A, 7B, and 7C and 8A, 8B, and 8C, respectively. In the embodiment 700 illustrated in FIGS. 7A, 7B, and 7C, the grip member 722 is pivotally connected to the housing 702 at pivot point 723, and it is linked to sector gear 732 by means of linkage member 730. The linkage member 730 is pivotally connected to the grip member 722 at pivot connection 758, but it (the linkage member 730) has a lost-motion connection with the sector gear 732 by virtue of an end 731 of the linkage member 730 being retained within, while being allowed to slide within, a lost-motion slot 737 in the side of the sector gear 732. Furthermore, the lost-motion slot 737 has a dogleg configuration, which facilitates the open-to-cock nature to the injection device 700.

Figure 7A:
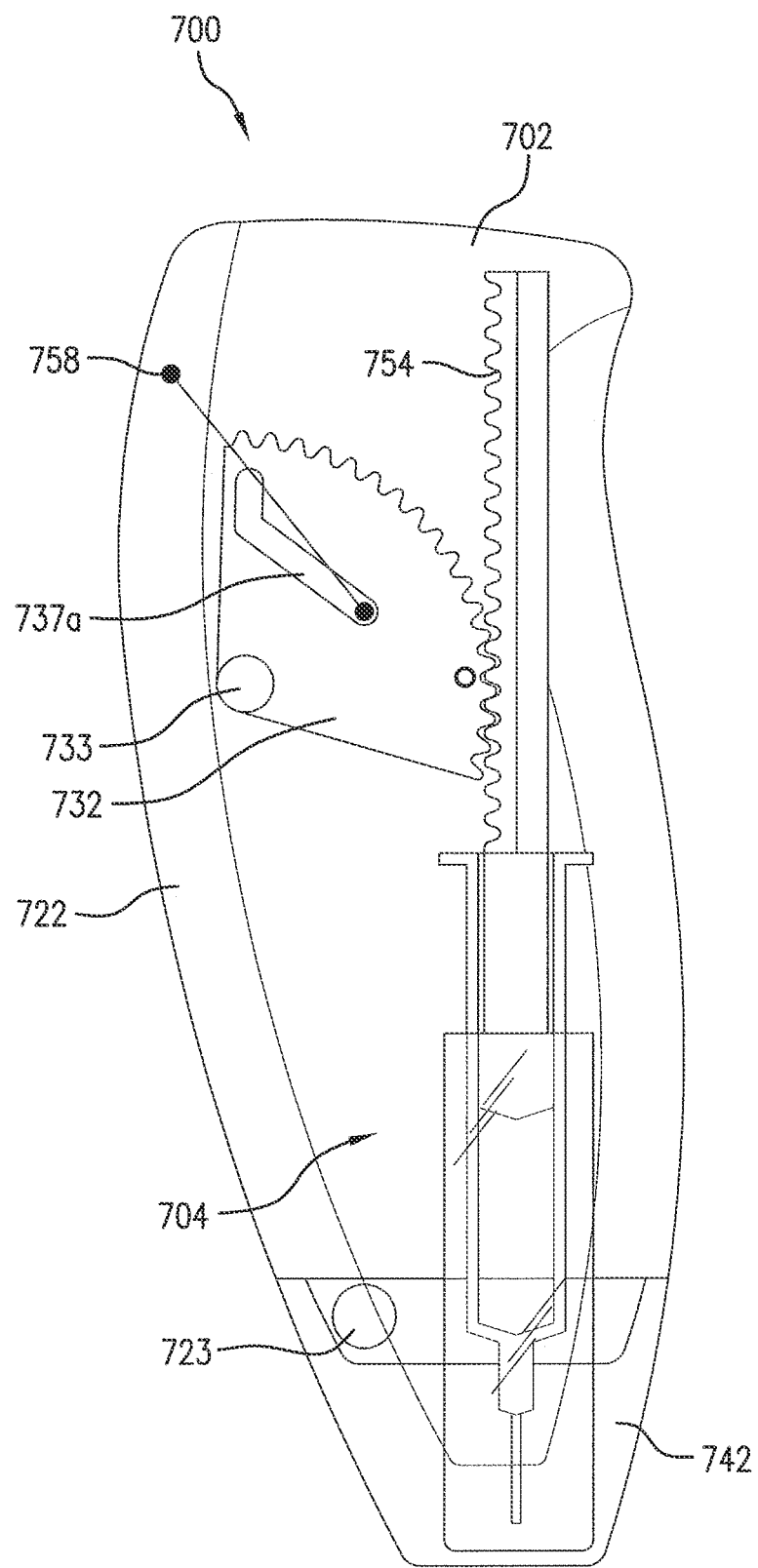
FIGS. 7A, 7B, and 7C are schematic side views illustrating internal components of a seventh embodiment of an injection device according to the invention as the injection device is used to inject medication into a patient.
Figure 7B:
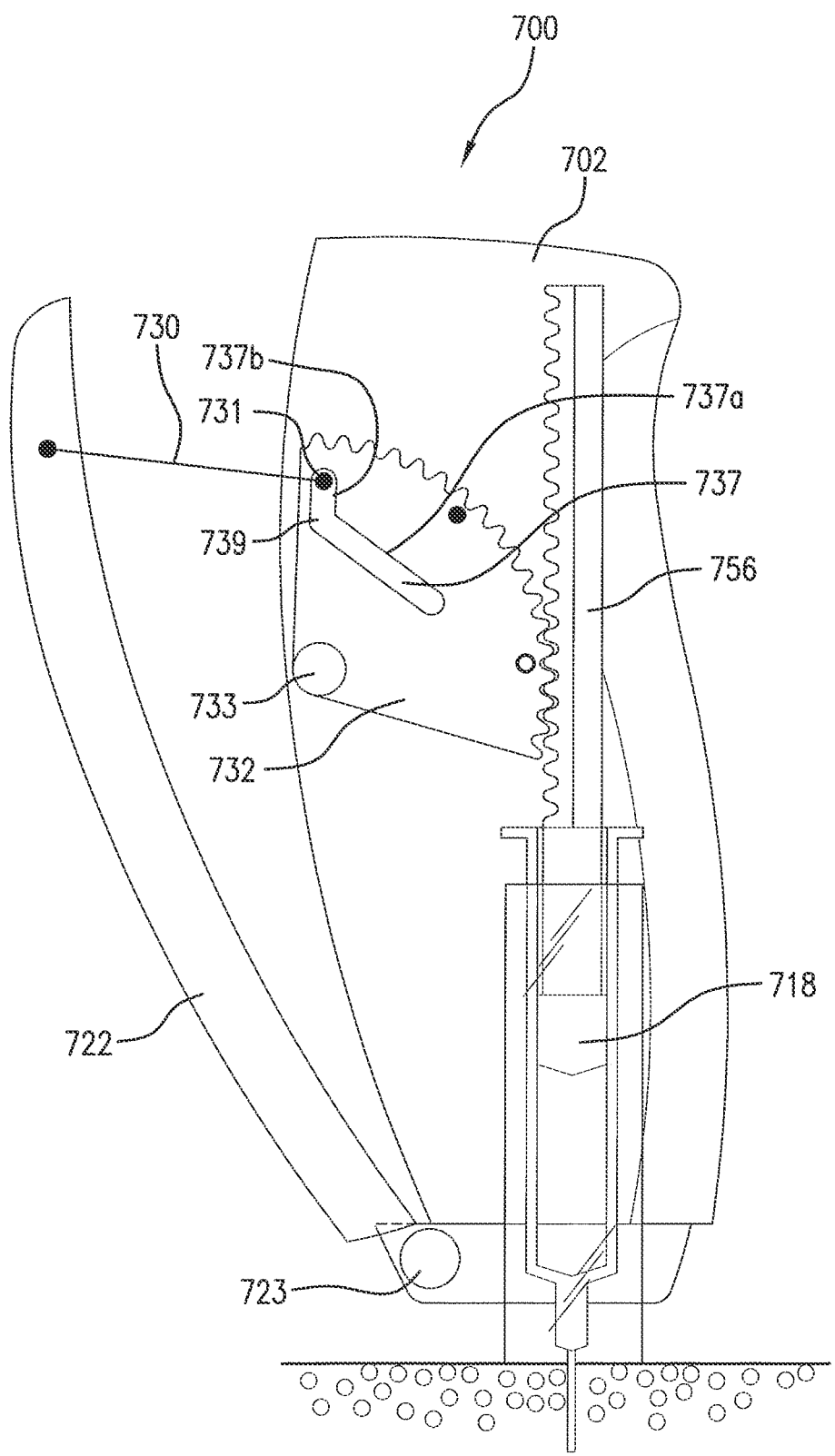
Figure 7C:
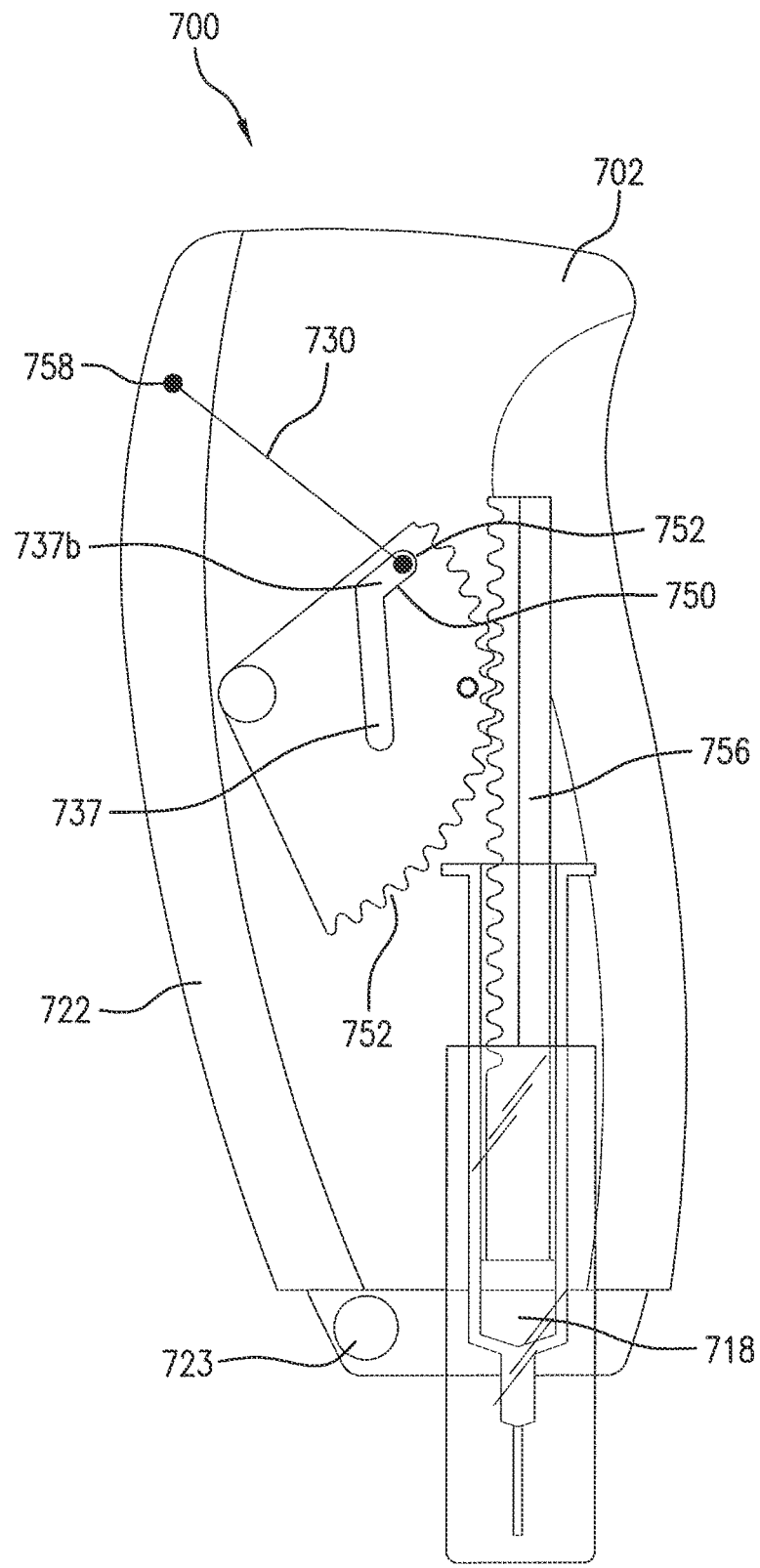

When the injection device 700 is in its "primed," ready-to-use configuration, the grip member 722 will be pivoted closed, in engagement with the housing 702, as shown in FIG. 7A. To use the device 700, cover 742 is removed from the housing 702 and the grip member 722 is rotated away from the housing 702 to the extended position shown in FIG. 7B, to "cock" the device 700 for injection. As the grip member 722 pivots away from the housing 702, the end 731 of the linkage member 730 slides along one leg 737a of the lost-motion slot 737. Furthermore, the linkage member 730 is rotationally biased, e.g., by means of a coil spring (not illustrated) disposed around the pivot connection 758. Therefore, once the end 731 of the linkage member 730 reaches the vertex 739 between the two legs 737a and 737b of the lost-motion slot 737, the end 731 of the linkage member will snap into the second leg 737b of the lost-motion slot 730, to assume the position shown in FIG. 7B. At this point, the injection device 700 is "cocked" and ready for the medication contained therein to be discharged.

To discharge the medication, the grip member 722 is squeezed toward the housing 702. As the grip member 722 pivots toward the housing 702, the end 731 of the linkage member 730 bears against the front surface 750 and/or the end 752 (FIG. 7C) of the lost-motion slot 737, thereby driving the sector gear 732 to pivot around pivot axis 733.

As the sector gear 732 rotates, the teeth 752 along its periphery, which engage with teeth 754 along pinion rod 756, drive the pinion rod 756 downwardly, thereby causing the piston 718 to pressurize and inject medication contained within the syringe assembly 704 into the patient.

Figure 8A:
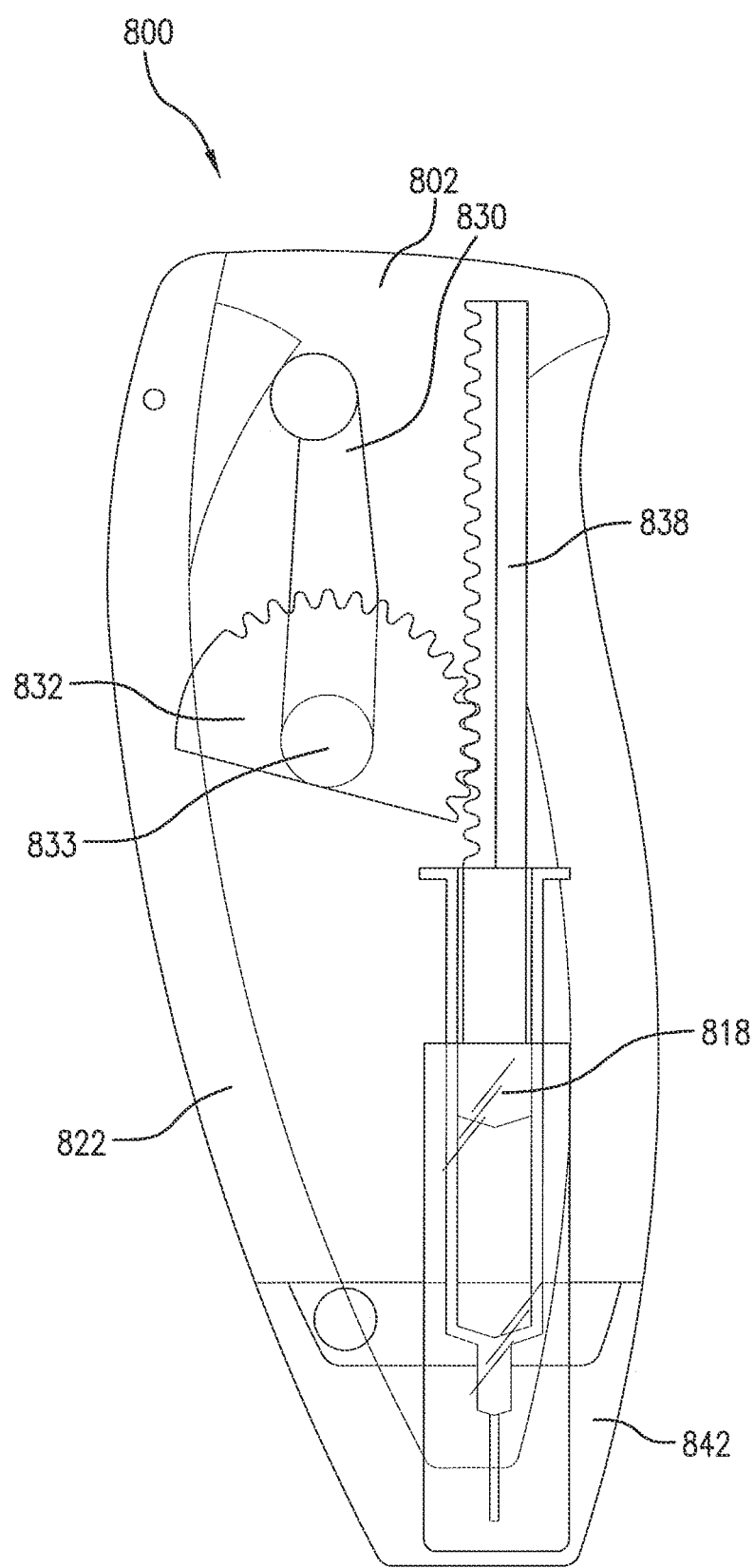
FIGS. 8A, 8B, and 8C are schematic side views illustrating internal components of an eight embodiment of an injection device according to the invention as the injection device is used to inject medication into a patient.
Figure 8B:
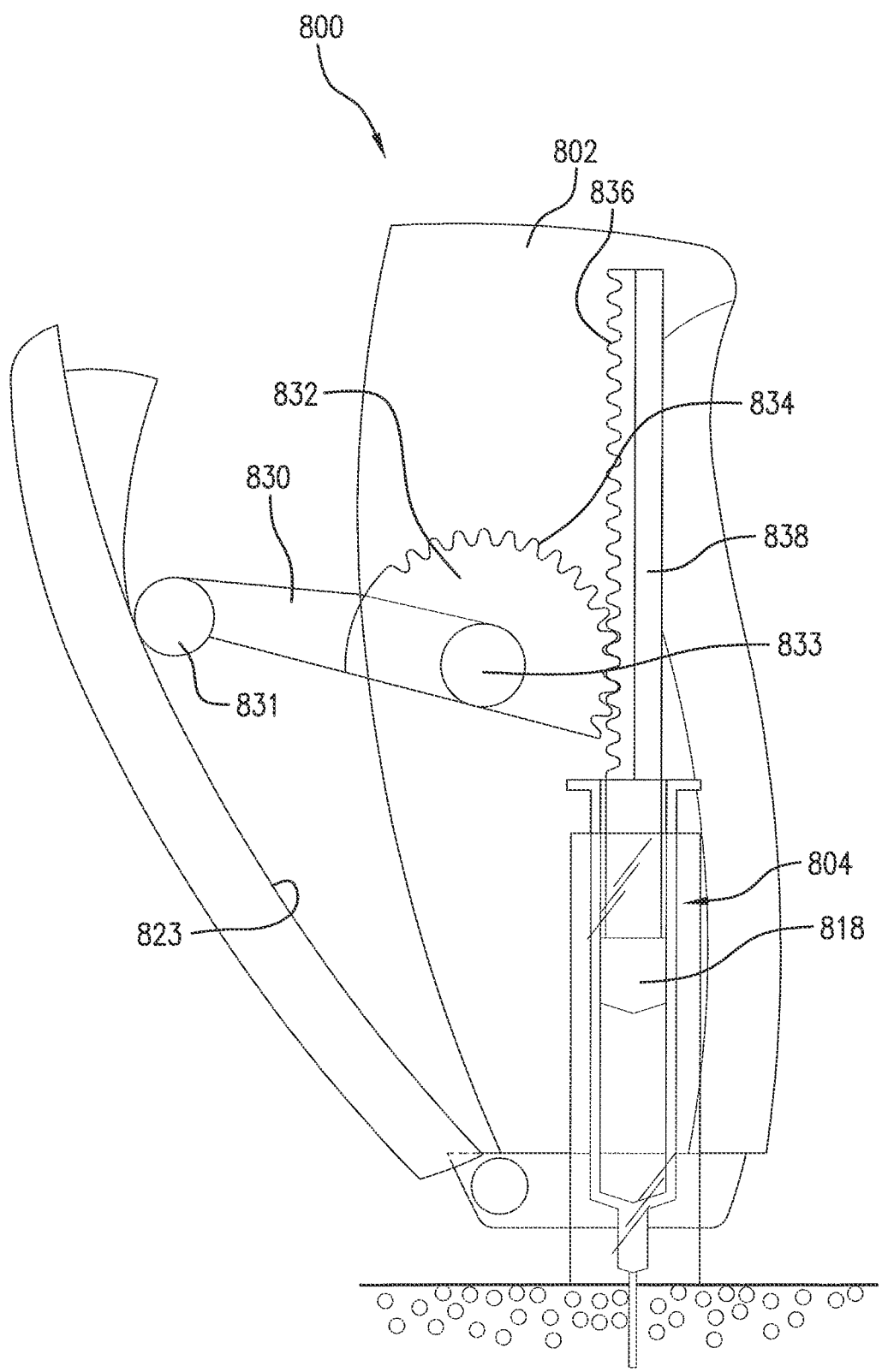
Figure 8C:
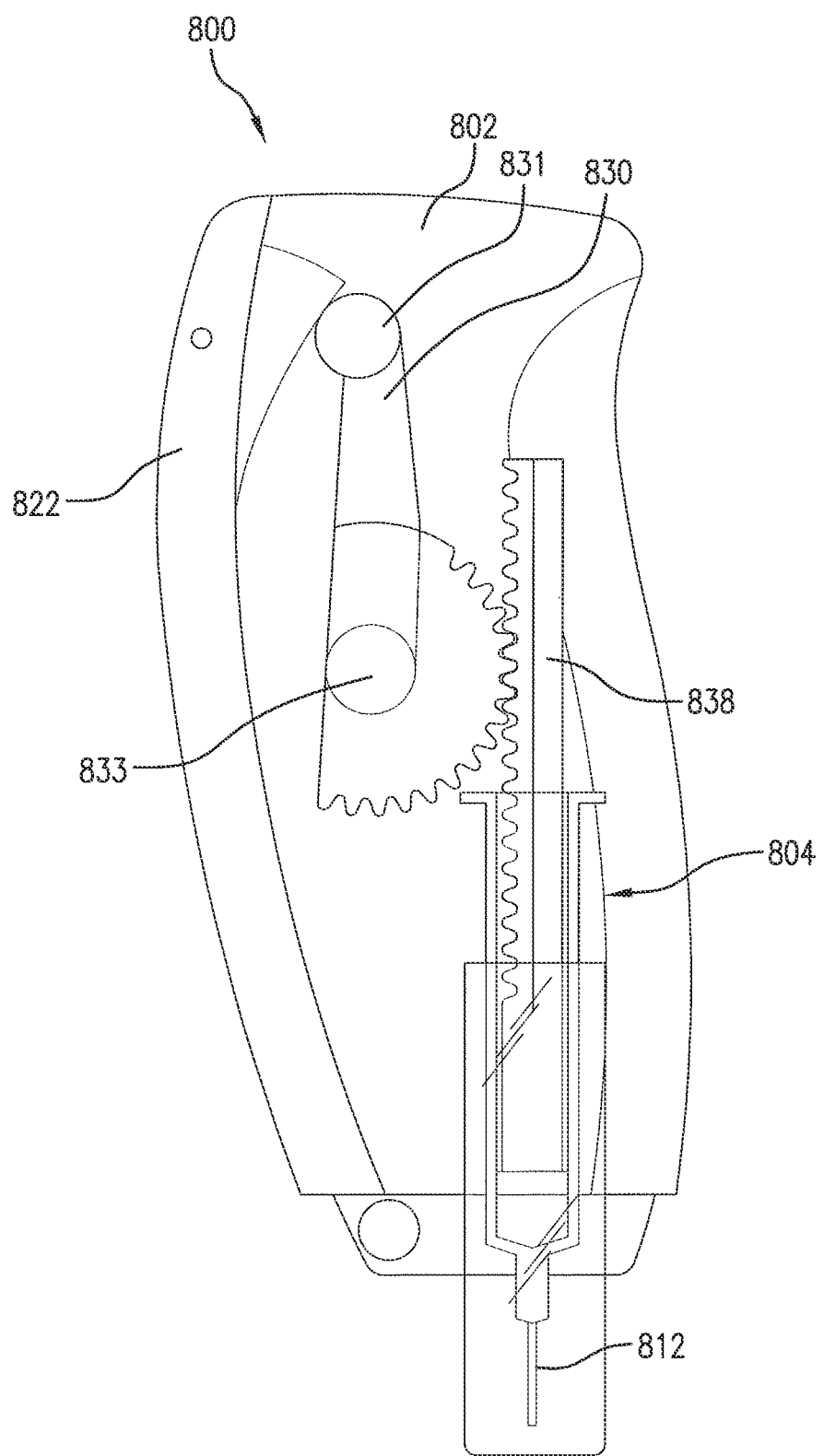

As illustrated in FIGS. 8A, 8B, and 8C, in place of the linkage member 730, the embodiment 800 has a flip-out roller arm 830 to transfer force from the grip member 822 to the piston 818. The roller arm 830 shares a pivot axis 833 with sector gear 832, and it is rotationally biased relative to the sector gear 832, e.g., via a coil spring (not shown), so as to rotate outwardly relative to the sector gear 832 (i.e., counterclockwise as illustrated in the figures). Therefore, when the grip member 822 is pivoted outwardly to the position shown in FIG. 8B, the roller arm 830 "follows along" by also pivoting outwardly, with roller member 831 at the end of the roller arm 830 rolling along the inner surface 823 of the grip member 822. Suitably, closure cap 842 blocks the grip member 822, so as to prevent it from being forced outwardly by the roller arm 830 before the injection device is ready to be used; alternatively, an overwrap or band could be provided around the injection device 800 for the same reason. When the roller arm 830 reaches the fully extended position shown in FIG. 8B, it locks in place relative to the sector gear 823, e.g., by means of a flexural tab on the roller arm 830 (not illustrated) engaging with a slot on the side of the sector gear 832 (not illustrated).

Medication contained within the injection device 800 is then injected by squeezing the grip member 822, thereby causing it to pivot back toward the housing 802. As the grip member 822 pivots, it applies force to the roller arm 830; the roller arm 830 in turn, which is locked relative to the sector gear 832, forces the sector gear 832 to rotate. As the sector gear 832 rotates, its teeth 834, which are engaged with corresponding teeth 836 formed along the side of rack member 838, drive the rack member 838 downwardly, thereby depressing piston 818 and causing the medication contained within the syringe assembly 804 to be injected into the patient.

Notably, because the roller member 831 only bears against the inner surface 823 of the grip member 822 without the roller arm 830 being connected to the grip member 822 in a way that restrains it (the roller arm), and because the roller arm 830 locks in place relative to the sector gear 832 once the roller arm reaches its fully extended position shown in FIG. 8B, the sector gear 832 and roller arm 830 will remain in the position shown in FIG. 8C even if the grip member 822 is pivoted outwardly once more, after the medication has been discharged. This prevents substances from being drawn back into the syringe 804 via the hypodermic needle 812 once the medication originally present in the injection device 800 has been discharged. In other words, this feature prevents the injection device 800 from being reused.

In the embodiments described thus far, the force-transfer mechanisms are all configured such that forces are transmitted in compression, i.e., by pushing. It is possible, however, for at least some of the forces to be transferred in tension, i.e., by pulling on one or more force-transferring members.

Figure 9A:
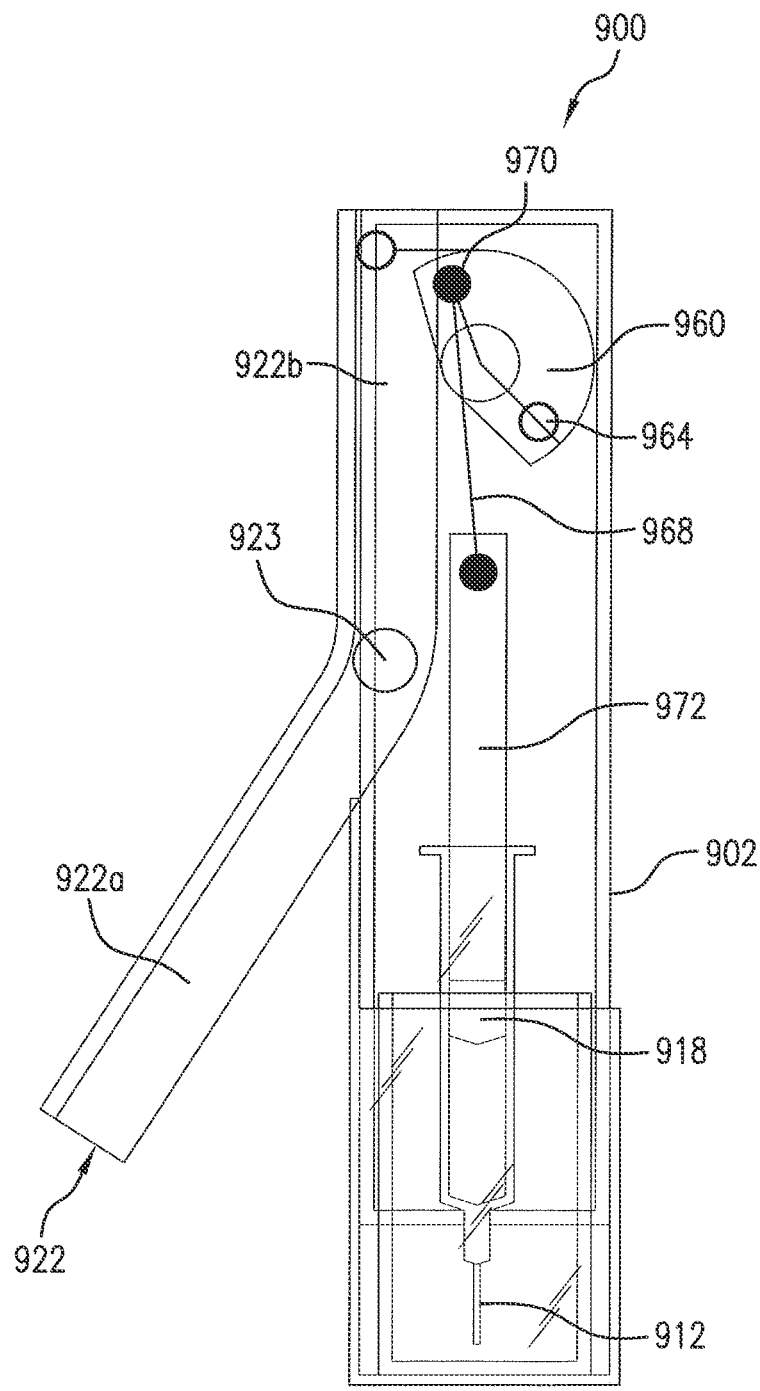
FIGS. 9A, 9B, and 9C are schematic side views illustrating internal components of a ninth embodiment of an injection device according to the invention as the injection device is used to inject medication into a patient.
Figure 9B:
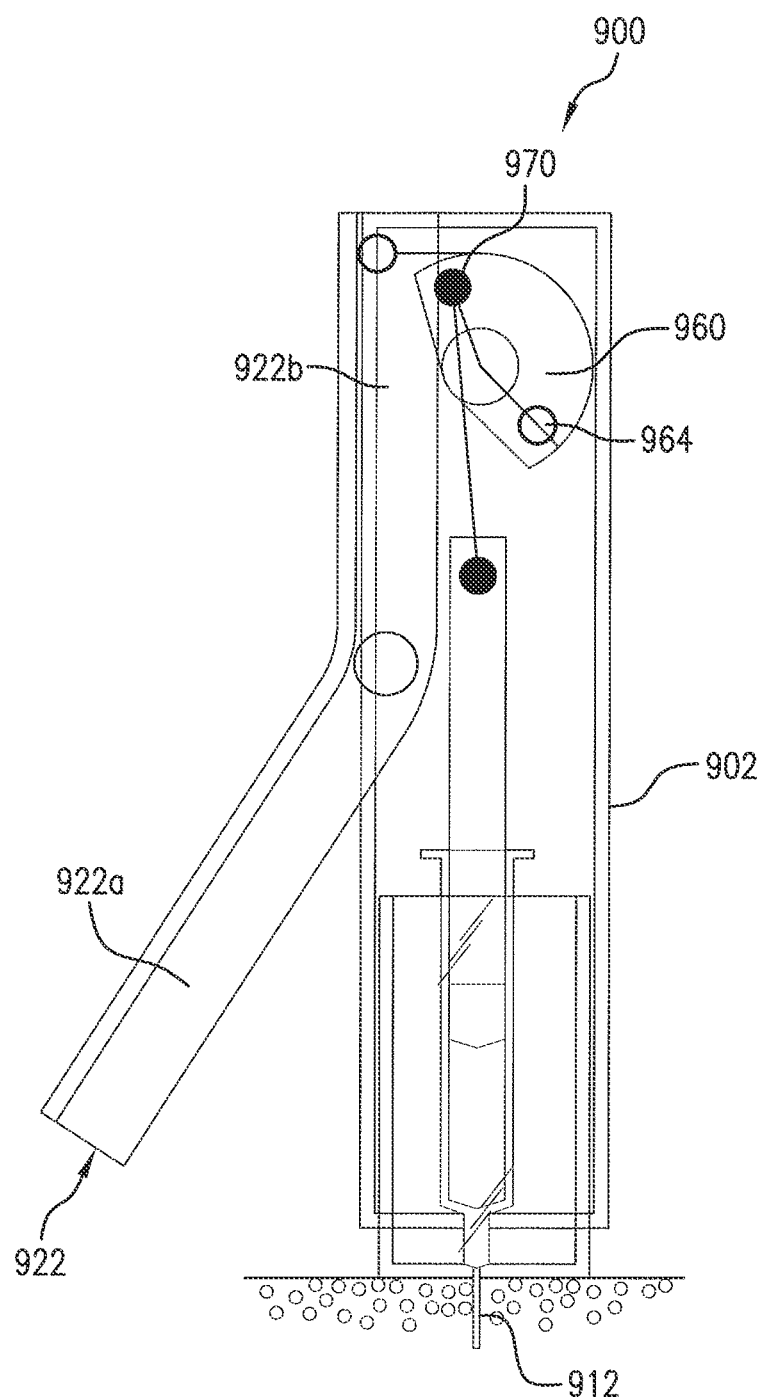
Figure 9C:
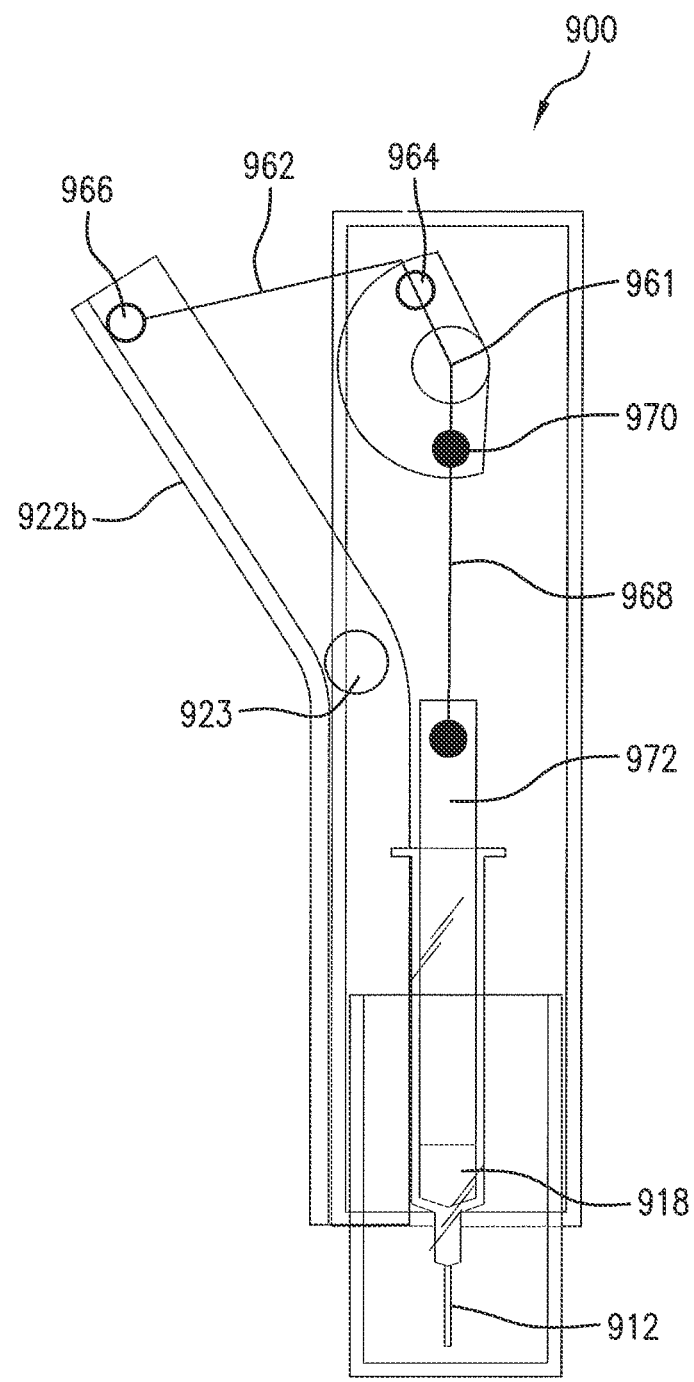

For example, the embodiment 900 of an injection device illustrated in FIGS. 9A, 9B, and 9C utilizes both tension and compression to transfer forces. In particular, this embodiment 900 has a rotating cam member 960 as part of the force-transfer mechanism. A flexible strap 962 is anchored to the cam member 960 at one point 964; it wraps around the curved periphery of the cam member 960; and it is anchored to the bell crank-shaped grip member 922 at another point 966. Additionally, push rod 968 is pivotally connected to the cam member 960 at point 970, and it is pivotally connected to plunger 972 at point 974.

With this embodiment 900 of an injection device according to the invention, medication is discharged by squeezing the lower leg 922a of the grip member 922 toward the housing 902. This causes the grip member 922 to pivot about pivot point 923, thereby causing the upper leg 922b of the grip member 922 to pivot away from the housing 902. As the upper leg 922b of the grip member 922 pivots away from the housing 902, it pulls on the strap 962, which causes the cam member to rotate about its pivot axis 961. As the cam member 960 rotates, it pushes push rod 968 downwardly, thereby depressing plunger 972 and piston 918 so as to pressurize medication contained within the syringe and cause it to be injected.

Notably, because the strap 962 is flexible, it transmits force in tension but not in compression. Therefore, once the medication has been injected and the cam member 960 has moved to the position shown in FIG. 9C, pivoting the grip member 922 back to the position shown in FIG. 9A will simply cause the strap 962 to buckle or fold in on itself instead of forcing the cam member 960 back to the position shown in FIGS. 9A and 9B. This, then, prevents the plunger 972 from being withdrawn from the syringe and, accordingly, substances from being drawn into the syringe via the needle 912. In other words, the flexible, non-compressive-force-transmitting nature of the strap 962 renders the injection device 900 single-use in nature.

Figure 10B:
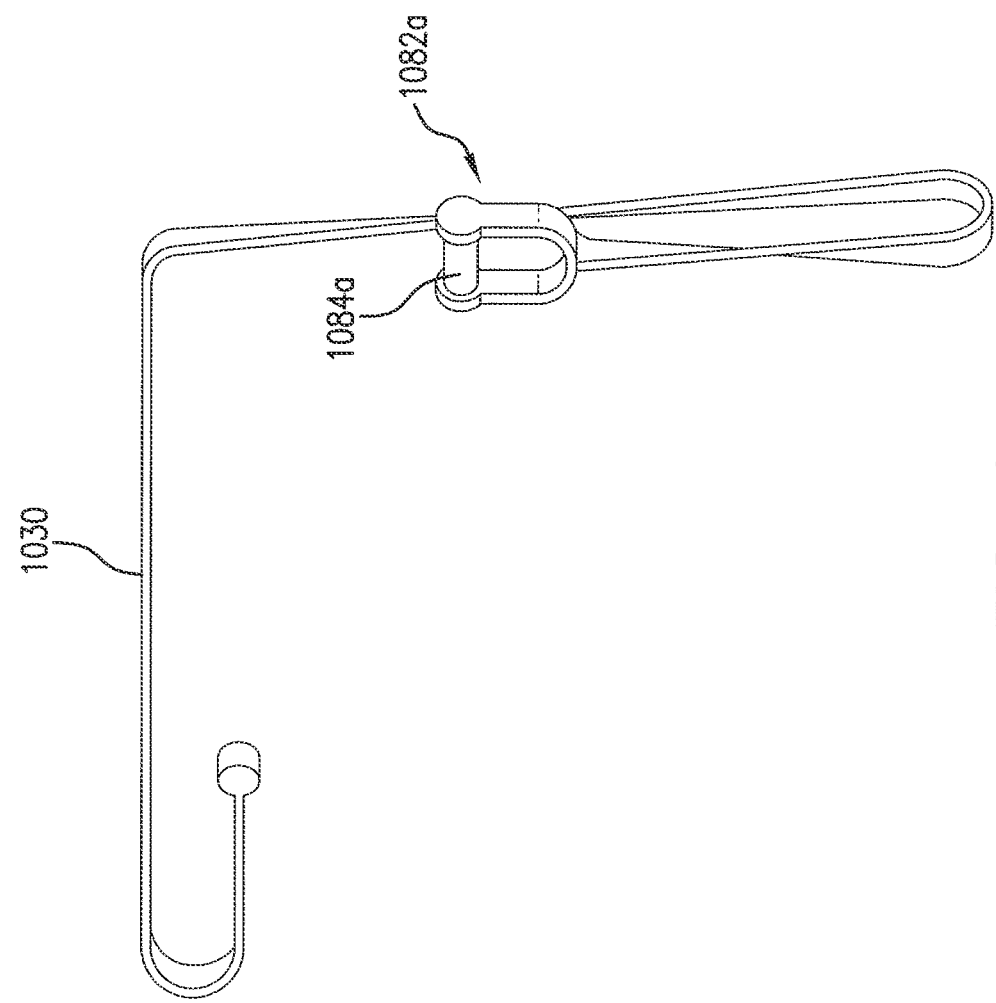
FIG. 10A is a schematic perspective view illustrating internal components of a tenth embodiment of an injection device according to the invention, with FIG. 10B providing an enlarged view of certain components thereof.
Figure 10A:
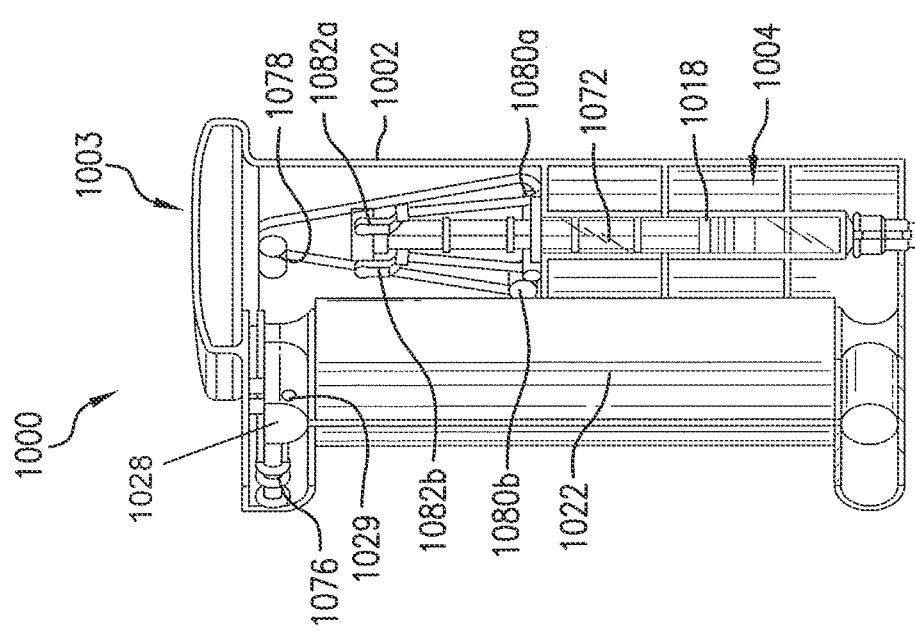

Finally, it is possible to configure an injection device according to the invention to transmit forces from the grip member to the push member entirely via tension if so desired. For example, in the embodiment 1000 of an injection device illustrated in FIGS. 10A and 10B, a pair of flexible straps 1030 is used to transmit squeezing force from the grip member 1022 to the plunger 1072 and piston 1018 of syringe assembly 1004. In particular, one end of each strap 1030 is anchored to the upper guide lug 1028 at anchor point 1029. The straps 1030 extend outwardly from the guide lug 1028 (i.e., away from the medication portion 1003 of the housing 1002); pass around post 1076 to "double back" on themselves; and pass over post 1078. The straps 1030 then extend downwardly within the medication portion 1003 of the housing 1002, with one of the straps looping around post 1080a to double back upwardly on itself and the other strap looping around post 1080b to double back upwardly on itself. Finally, each of the straps 1030 terminates in a stirrup fitting 1082a, 1082b, which are pivotally attached to the top of the plunger 1072 via stirrup cross-pins, e.g. 1084a, as illustrated in FIG. 10A for one of the two straps 1030. Thus, squeezing the grip member 1022 toward the housing 1002 causes the grip member 1022 to pull on the straps 1030, which pull on and transmit downward-acting force to the plunger entirely through tension. Furthermore, moving the grip member 1022 back to the position shown in FIG. 10A will have no effect in terms of causing the plunger 1072 to be withdrawn from the syringe assembly 1004, since the straps 1030 do not transmit force via compression. Therefore, the flexible, non-compressive-force-transmitting nature of the straps 1030 renders the injection device 1000 single-use in nature, too.

The foregoing disclosure is only intended to be exemplary of the methods and products of the present invention. Departures from and modifications to the disclosed embodiments may occur to those having skill in the art. The scope of the invention is set forth in the following claims.

We claim:

1. An injection device for injecting medication into the body of a patient, comprising:
   a housing with a medication-receiving chamber disposed therein, the medication-receiving chamber having a medication discharge port;
   a push member disposed within the housing and arranged to move in a direction that causes medication contained within the medication-receiving chamber to be pressurized;
   a grip member moveably connected to the housing; and
   a force-transfer mechanism operatively coupling the grip member and the push member;
   wherein the medication-receiving chamber and the medication discharge port are configured and arranged such that when the housing is held across the palm of a medication-administering person's hand with the grip member positioned to be engaged by the administering person's non-thumb fingers in a squeezing motion, pressurization of medication within the medication-receiving chamber will cause the medication to be discharged, via the medication discharge port, in a direction toward the outer, blade edge of the device-holding hand;
   wherein the grip member is connected to the housing in a manner such that said squeezing motion on the grip member causes at least a portion of the grip member to move toward the housing;
   wherein the force-transfer mechanism is arranged to transfer movement of the grip member, caused by squeezing the grip member with a first, net amount of force, to the push member so as to pressurize medication contained within the medication-receiving chamber with a second amount of force and cause the medication to be discharged via the medication discharge port;
   wherein the force-transfer mechanism includes at least one component configured for lost motion; and
   wherein components of the injection device, including the component configured for lost motion, are configured and arranged to provide the injection device with
   1) a packaged configuration in which the grip member lies flush with the housing;
   2) a ready-for-use configuration in which the grip member has been moved away from the packaged configuration and away from the housing, at which point movement of the grip member back toward the housing will cause the force-transfer mechanism to cause the push member to pressurize the medication contained within the medication-receiving chamber to cause the medication to be discharged via the medication discharge port; and
   3) a spent configuration in which the push member has moved to a terminal end of its range of travel to discharge the medication, at which terminal end of its range of travel the push member is inaccessible to the user for manual retraction and the component configured for lost motion prevents the push member from being moved in a retraction direction whereby the injection device is configured for single use.

2. The injection device of claim 1, wherein the force-transfer mechanism is arranged with, or so as to produce during medication-injecting movement, a plurality of moment arms, whereby the second amount of force that is applied to the push member to pressurize and discharge the medication is greater than the first, net amount of force that is applied to the grip member.

3. The injection device of claim 1, wherein the grip member is pivotally attached to the housing, at an attachment point, such that the portion of the grip member to which force is applied when the grip member is being squeezed pivots toward the housing.

4. The injection device of claim 3, wherein the grip member is pivotally attached to the housing at an end portion of the grip member, such that the entire grip member pivots toward the housing when the grip member is being squeezed.

5. The injection device of claim 1, wherein the force-transfer mechanism comprises a plurality of discrete elements through which a force-transmission pathway extends.

6. The injection device of claim 1, wherein the force-transfer mechanism is configured to transmit force from the grip member to the push member entirely in compression.

7. The injection device according to claim 1, wherein the component configured for lost motion comprises a pair of ratchet components that slip past each other in one direction and that lockingly engage each other in an opposite direction.

8. The injection device according to claim 1, wherein the component configured for lost motion comprises a slotted pinion gear.

9. The injection device according to claim 1, wherein the component configured for lost motion comprises a linkage member that bears against the grip member when the grip member is moved in one direction but that loses contact with the grip member when the grip member is moved in an opposite direction.

* * * * *